(12) United States Patent
Demmer et al.

(10) Patent No.: US 9,433,904 B2
(45) Date of Patent: *Sep. 6, 2016

(54) CELLULOSE HYDRATE MEMBRANE, METHOD FOR THE PRODUCTION THEREOF, AND USE THEREOF

(75) Inventors: Wolfgang Demmer, Göttingen (DE); René Faber, Göttingen (DE); Hans-Heinrich Hörl, Bovenden (DE); Csilla Kiss, Göttingen (DE); Dietmar Nußbaumer, Göttingen (DE)

(73) Assignee: SARTORIUS STEDIM BIOTECH GMBH, Göttingen (DE)

( * ) Notice: Subject to any disclaimer, the term of this patent is extended or adjusted under 35 U.S.C. 154(b) by 814 days.

This patent is subject to a terminal disclaimer.

(21) Appl. No.: 12/937,847

(22) PCT Filed: Feb. 10, 2009

(86) PCT No.: PCT/EP2009/000913
§ 371 (c)(1),
(2), (4) Date: Mar. 4, 2011

(87) PCT Pub. No.: WO2009/127285
PCT Pub. Date: Oct. 22, 2009

(65) Prior Publication Data
US 2011/0147292 A1    Jun. 23, 2011

(30) Foreign Application Priority Data

Apr. 14, 2008  (DE) .................. 10 2008 018 719
Nov. 4, 2008   (DE) .................. 10 2008 055 821

(51) Int. Cl.
*B01D 71/12*    (2006.01)
*B01D 67/00*    (2006.01)
(Continued)

(52) U.S. Cl.
CPC ........... *B01D 67/0093* (2013.01); *B01D 69/02* (2013.01); *B01D 71/10* (2013.01);
(Continued)

(58) Field of Classification Search
None
See application file for complete search history.

(56) References Cited

U.S. PATENT DOCUMENTS

| 6,103,121 A | 8/2000 | Bhattacharyya et al. |
| 2004/0069707 A1 | 4/2004 | Naldrett |

(Continued)

FOREIGN PATENT DOCUMENTS

| DE | 4323913 A1 | 1/1995 |
| DE | 10 2004 053 787 A1 | 5/2006 |
| EP | 0586268 B1 | 2/2000 |
| WO | WO 03/015902 A2 | 2/2003 |

(Continued)

OTHER PUBLICATIONS

International Search Report dated May 27, 2009, for International Application No. PCT/EP2009/000913.

(Continued)

*Primary Examiner* — Krishnan S Menon
(74) *Attorney, Agent, or Firm* — Knobbe, Martens, Olson & Bear LLP

(57) ABSTRACT

There is provided a cellulose hydrate membrane having a porous double structure which consists of micropores having a diameter in the range from >100 nm to 20 μm and ultrapores which have a diameter of <100 nm and which are not accessible to Blue Dextran having an average molecular weight Mw of 2 000 000, wherein the fraction of the volume of the ultrapores is more than 15% of the entire pore volume accessible to water. In addition, a method for producing the membrane, its use as an adsorption membrane, and an apparatus for membrane chromatography are specified.

38 Claims, 7 Drawing Sheets

Figure 1:
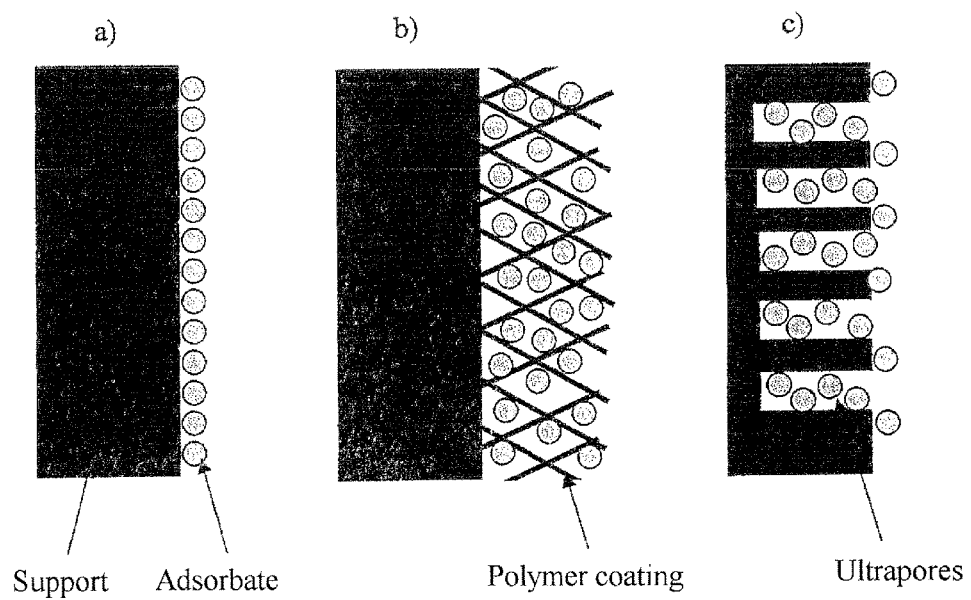

(51) Int. Cl.
*B01D 69/02* (2006.01)
*B01D 71/10* (2006.01)
*B01J 20/26* (2006.01)
*B01J 20/28* (2006.01)
*B01J 20/285* (2006.01)
*B01J 20/286* (2006.01)
*C07K 1/30* (2006.01)

(52) U.S. Cl.
CPC ........... *B01J 20/262* (2013.01); *B01J 20/265* (2013.01); *B01J 20/267* (2013.01); *B01J 20/285* (2013.01); *B01J 20/286* (2013.01); *B01J 20/28033* (2013.01); *B01J 20/28069* (2013.01); *B01J 20/28078* (2013.01); *C07K 1/30* (2013.01); *B01D 2323/16* (2013.01); *B01D 2323/30* (2013.01); *B01D 2323/36* (2013.01); *B01D 2325/02* (2013.01); *B01D 2325/12* (2013.01); *B01D 2325/14* (2013.01); *B01D 2325/16* (2013.01)

(56) References Cited

U.S. PATENT DOCUMENTS

2007/0244307 A1 10/2007 Engstrand
2008/0179248 A1 7/2008 Axen
2010/0059440 A1* 3/2010 Rudstedt et al. ............. 210/651

FOREIGN PATENT DOCUMENTS

| WO | 2007017085 A3 | 2/2007 |
| WO | WO 2007/017085 A2 | 2/2007 |
| WO | WO 2008/095709 A1 | 8/2008 |

OTHER PUBLICATIONS

Hermanson, et al., "Immobilized Affinity Ligand Techniques", Academic Press, Inc., San Diego, 1992, in 104 pages. (Duo to the large file size, this document is divided and filed in three separate parts).

* cited by examiner

Lysozyme bound to the adsorptively active polymer layer

Membrane-penetrating micropores

Coarse structure of relatively thick fibers of the cellulose or their agglomerates, adsorptively inactive More finely distributed fibroid or clusterlike membrane material Membrane-penetrating micropores Coarse structure of relatively thick fibers of the cellulose or their agglomerates, with bound lysozyme More finely distributed fibroid or clusterlike membrane material, with bound lysozyme Membrane-penetrating micropores Coarse structure of relatively thick fibers of the cellulose or their agglomerates with ultrapores accessible to biomolecules,with bound lysozyme More finely distributed fibroid or clusterlike membrane material with ultrapores accessible to biomolecules,with bound lysozyme

CELLULOSE HYDRATE MEMBRANE, METHOD FOR THE PRODUCTION THEREOF, AND USE THEREOF

This application is the U.S. National Phase of International Application No. PCT/EP2009/000913, filed Feb. 10, 2009, designing the U.S. and published in German as WO 2009/127285 on Oct. 22, 2009 which claims the benefit of German Patent Application Nos. 10 2008 018 719.4, filed Apr. 14, 2008 and 10 2008 055 821.4, filed Nov. 4, 2005.

The following invention relates to a cellulose hydrate membrane, methods for its production, and the use thereof as an adsorption membrane.

The following definitions and facts underlie the description of the invention, wherein "flow rate" is understood to mean hydraulic permeability.

Flat adsorbents with pores passing from one side to the other side are referred to as adsorption membranes. Adsorbents are porous solids which can selectively form bonds with certain components of fluids via functional surface groups referred to as ligands. Target substance(s) and/or contaminant(s) are, according to the invention, referred to as adsorbates, and they can also be various different substances. Adsorbates can be single molecules, associates, or particles which are, in each case, preferably proteins or other substances of biological origin.

With regard to ligands which interact with the adsorbate(s), mention can be made, by way of example, of ion exchangers, chelating agents and heavy metal chelates, thiophilic, hydrophobic ligands of various chain lengths and configurations, reversed-phase systems, dye ligands, affinity ligands, amino acids, coenzymes, cofactors and their analogs, substrates and their analogs, endocrine and exocrine substances, such as hormones and active ingredients acting like hormones, effectors and their analogs, enzyme substrates, enzyme inhibitors and their analogs, fatty acids, fatty acid derivatives, conjugated fatty acids and their analogs, nucleic acids, such as DNA, RNA, and their analogs and derivatives (single-, double-, and/or multistranded), and also peptide nucleic acids and their derivatives, viruses, virus particles, monomers and their analogs and derivatives, oligomers to polymers and their analogs and derivatives, high-molecular-weight carbohydrates, which can be linear or branched, unsubstituted or substituted, polymeric glycoconjugates, such as heparin, amylose, cellulose, chitin, chitosan, and their monomers and oligomers and derivatives and analogs thereof, lignin and its derivatives and analogs, other biochemical ligands, such as oligopeptides and polypeptides, e.g., proteins and their oligomers, multimers, subunits and also parts thereof, more particularly lectins, antibodies, fusion proteins, haptens, enzymes, and subunits and also parts thereof, structural proteins, receptors and effectors and also parts thereof, and in addition xenobiotics, pharmaceuticals and pharmaceutical active ingredients, alkaloids, antibiotics, biomimetics, etc.

An adsorbent can, at the same, also carry two or more types of functional groups on its inner and outer surface.

The binding of the adsorbates to the adsorbent can be reversible or irreversible; in any case, it makes possible their separation from the fluids, which are generally aqueous liquids and referred to hereinafter as media. The term "elution" summarizes the desorption and the accompanying rinse steps, etc., and the liquid used for elution is the "eluent". The components can represent one or more target substances and/or one or more contaminants. "Target substances" are valuable materials which are to be recovered in an enriched or pure form from the medium. Target products can, for example, be recombinant proteins, such as, for example, monoclonal antibodies. "Contaminants" are materials whose absence or removal from the fluid is required or desirable for technical, regulatory, or other reasons. Contaminants can, for example, be viruses, proteins, amino acids, nucleic acids, endotoxins, protein aggregates, ligands, or parts thereof. For the removal of contaminants, which is referred to as "negative adsorption", the adsorption can (may) proceed irreversibly when the adsorbent is to be used only once. In the case of adsorption of target substance(s), the process must proceed reversibly. Either a mere enrichment or a separation into multiple target substances can be carried out, in which latter case either the adsorption, the desorption, or both can take place selectively.

The process is referred to as adsorptive material separation or chromatography. Conventional adsorbents for chromatography are in particulate form and are used in the form of packings in columns. In contrast to this, adsorption membranes are generally employed in modules whose designs correspond to the modules which are usually customary in membrane filtration (e.g., spiral-wound module, stack module, etc.). The requirements for mechanical strength are comparable with those to be applied to filtration membranes and are thus substantially higher than for particulate adsorbents, for which fragile support materials, such as gels of dextran or agarose, have established themselves so universally that the term "gels" has become established as a synonym for them. In contrast, there is the same basic requirement for all membranes and gels, this being very low nonspecific adsorption.

The implementation of chromatographic separation with the help of adsorption membranes is also referred to as membrane chromatography, and all of the synthetic and natural ligands known in chromatography can also be used in the same way for adsorption membranes. The bonding of the ligand to the support can be preceded by an "activation" of the support, i.e., the introduction of reactive, functional groups which are capable of spontaneous bonding of the ligand. In rarer cases, the ligand itself has a reactive group, such as, for example, the reactive dyes, serving as dye ligands, from the textile industry. Techniques for bonding functional groups are known per se to a person skilled in the art (e.g., from Greg T. Hermanson, A. Krishna Mallia, Paul K. Smith, Immobilized Affinity Ligand Techniques, Academic Press, INC, 1992).

The amount of adsorbate, based on the amount of the adsorbent, which becomes bound per loading in equilibrium with the medium, i.e., the specific binding capacity of the adsorbent, is, for a given ligand density, proportional to its specific surface area. The specific surface area of porous structures increases with decreasing pore size; as a result, its specific binding capacity also increases, provided that the exclusion limit of the pores, i.e., that molar mass below which entry of a molecule is possible, does not fall below the molar mass of the adsorbate.

Adsorption membranes offer, in contrast to particulate adsorbents, the possibility of forcing perfusion with the medium by applying a hydraulic pressure difference between the two sides of their surface, whereby, instead of purely diffusive transport of the adsorbates in the direction of a concentration gradient into the interior of the adsorbent, convective trans-port is achieved, which can take place very much faster at a high flow rate. As a result, a disadvantage inherent to particulate adsorbents, which is referred to as "diffusion limitation", can be avoided, which consists in a considerable increase in the time required for establishing the adsorption equilibrium with increasing particle size of the adsorbent and increasing molar mass of the adsorbate, causing a worsening of the kinetics.

However, the utilization of convective material transport with adsorption membranes reaches a limit, in that the effects of the pore size on the binding capacity and the flow rate are contrary: the flow rate increases with increasing pore size, but the binding capacity, as mentioned, decreases. The separation capacity of porous adsorption membranes depends on both the pore structure of the base membrane and the type, amount, and distribution of functional groups in this pore structure. In contrast to filtration membranes, whose performance is determined mainly by the structure of the membrane-penetrating pores, an ideal adsorption membrane thus features, in addition, a very large number of those pores which only slightly exceed the exclusion limit for the adsorbate and can also be dead-end pores, i.e., those pores which have only one single connection with a perfused area of the membrane. Such pores are not completely free from diffusion limitation, but exhibit this effect only to the extent to which material transport of the perfused area takes place by means of free diffusion. These different requirements for the pore structure are the main reason why an effective filtration membrane does not become an effective adsorption membrane solely by introducing appropriate ligands.

In the production of cellulose hydrate filtration membranes from cellulose ester membranes, the hydrolysis process is preferably carried out such that the porous structure of the membrane, as far as possible, does not change. This is achieved by measures which counteract swelling of the cellulose, e.g., by adding electrolytes or alcohols to the hydrolysis medium.

WO 2007/017085 A2 describes a method for producing crosslinked cellulose hydrate membranes, which consists in the simultaneous hydrolysis and crosslinking of cellulose ester membranes and is intended to be equally suitable for filtration and adsorption membranes. One of the goals of the invention described therein is the hydrolysis and crosslinking of the cellulose ester under conditions which do not affect the structure and permeability of the membrane. Since the structure of the membrane does not change in the simultaneous hydrolysis and crosslinking process, it can be assumed that the adsorption of adsorbates takes place at the surface of the micropores of the support, which corresponds to the surface of the starting cellulose ester membrane (cf. FIG. 1a).

Furthermore, the filtration, purification, or removal of biomolecules, such as proteins, amino acids, nucleic acids, viruses, or endotoxins, from liquid media is of great interest for the biopharmaceutical industry. Most applications of contaminant removal are currently run with conventional chromatography gels. The chromatography columns are distinctly oversized in order to achieve sufficient flow rates. The columns are reused, which means considerable expenditure on cleaning and validation. Adsorption membranes are already used in these processes when the adsorbates in the liquid phase are present at a very low concentration in relation to the capacity of the matrix, and so a large volume of the liquid phase can be processed per unit area of the matrix before the capacity is exhausted. Typical applications are in the area of negative adsorption, e.g., the removal of contaminants, such as DNA, viruses, host cell proteins (HCPs), Chinese hamster ovary proteins (CHOPs), endotoxins from antibody-comprising solutions, with positively charged membranes. Host cell proteins represent a broad spectrum of different cell proteins with different isoelectric points (pI) and different sizes and affinities for the adsorbent. The concentration and composition of the contaminants depend on the expression system and on the upstream purification steps. Typical concentrations of host cell proteins in a protein A pool are in the range of 500-5000 ppm (ng/mg antibody) and, after a further CEX step (cation exchanger step), in the range of 50-500 ppm. This corresponds to 0.5-5 g of host cell proteins per 10 kg of antibody. The binding capacities of anion exchange membranes known in the prior art, for example Sartobind® Q from Sartorius Stedim Biotech GmbH, are in the range of 20-50 g of bovine serum albumin (BSA) per l of membrane. In the case of use of a 5 l membrane adsorber, there is a 20-500-fold capacity excess. According to such a model calculation, the capacity of a membrane adsorber is sufficient to completely remove all host cell proteins after protein A/CEX steps. Owing to the broad spectrum of host cell proteins, of which some, depending on the operating conditions, are either not charged or have the same polarity as the adsorbent, immediate flow-through of host cell proteins often occurs at low utilization rates (about 1%) of the adsorbent.

EP 0 586 268 B1 describes a material for removing viruses from a protein-comprising solution, comprising a base material, a surface graft chain bonded to the base material, and a polyamine compound indirectly immobilized to the surface of the base material via the surface graft chain. EP 0 586 268 B1 discloses a selective removal of pathogenic substances, such as leukocytes, thrombocytes, and viruses, from body fluids, such as blood or plasma, wherein the disclosed material should adsorb no protein(s) from the body fluids. Polyamine compounds, such as spermidine, spermine, polyethyleneimines of varying molecular weight between MW 300 and 70 000, polyallylamine, Cationon UK, Panfix PX, or poly(N-benzylvinylpyridinium chloride), are immobilized on a grafted membrane, for example of polypropylene or polyvinylidene fluoride (PVDF). One application of the disclosed material is the selective removal of viruses from protein-comprising solutions. In the case of use of membranes on whose surface spermidine or polyethyleneimines are immobilized, removal rates of between 90% and 99.8% are reported for the phage ΦX174, for an HIV virus or for herpes virus I (H. F. strain) from human plasma (examples 5, 6, 7, and 8). If the polyamine functionalization of the material is omitted (comparative example 1) or quaternary ammonium groups are introduced into the graft chain, in which case polyamine functionalization is also omitted (comparative example 2), the membranes obtained only exhibit removal rates of between 50% and 99% for the herpes virus and ΦX174 from PBS buffer (buffer based on phosphate-buffered sodium chloride solution) and not more than 50% from human plasma.

Furthermore, no quantitative specifications for protein binding by the materials according to the invention are reported. The disclosed selectivity for virus depletion with an LRV (negative decadic logarithm of the retention capacity) of up to 3 logarithms relates only to the filtration of protein-comprising solutions, such as human plasma. It is to be expected that the described properties and advantages of the disclosed materials only relate to human plasma, but no general validity for other protein-comprising solutions can be claimed.

It is known from the prior art that membranes functionalized with quaternary ammonium groups are suitable for virus removal from protein solutions, e.g., in the purification of monoclonal antibodies. With membranes such as, for example, Sartobind® Q from Sartorius Stedim Biotech GmbH, LRVs of at least 5 are achieved.

WO 2008/008872 A2 describes membranes which are capable of irreversible binding of viruses with simultaneous electrostatic repulsion of basic proteins. Low-molecular-weight multimodal ligands which are immobilized on the membrane surface form strong interactions with a model phage ΦX174 and show LRVs of up to 5.9 (agmatine in table 2) at salt concentrations of up to 150 mM NaCl. The maximum binding capacities for the model protein bovine serum albumin are, however, only a maximum of 1000 mg/m$^2$, around a factor of 5-20 below the membrane adsorbers known in the prior art, e.g., Sartobind® Q. The data show that the claimed membranes show high virus depletion rates, but exhibit insufficient binding capacities for proteins for a broader application, e.g., contaminant removal from antibody solutions.

U.S. Pat. No. 7,396,465 B2 discloses positively charged microporous membranes, comprising a porous substrate, such as, for example, a polyethersulfone membrane or a membrane based on cellulose, and a crosslinked coating which is producible from polyamines and which has ammonium groups, wherein each ammonium group is covalently linked with the polymer backbone of the crosslinked coating by a polar spacer. Polyethyleneimines or copolymers of diallylamine derivatives and acrylic acid derivatives are some of the reactants used for the crosslinked coating.

US 2007/0256970 A1 discloses porous media which comprise porous polyethylene having at least one polymeric coating, wherein the at least one polymeric coating is crosslinked and is producible from a polyallylamine and from polyethyleneimines modified with epichlorohydrin.

Particulate ion exchanger gels which carry covalently bonded, polymeric amines on the surface of a porous base material are known in the prior art. U.-J. Kim, S. Kuga, Journal of Chromatography A, 955 (2002), 191-196, describes cellulose gels having immobilized polyallylamine which are producible through partial oxidation of cellulose with sodium periodate and through subsequent Schiff base formation with polyallylamine.

EP 1 224 975 B1 describes porous anion exchanger particles on whose surface a polyamine having a number-average molecular weight of at least 50 000 is bonded.

EP 0 343 387 B1 describes an assay system for macromolecules, consisting of microporous membranes having a cationic charge-modifying agent which is bonded to the entire wetted surface of the membrane, wherein the cationic charge-modifying agent is the reaction product of a polyamine with epichlorohydrin and comprises tertiary amine groups or quaternary ammonium groups and also epoxide groups along the polyamine chain. The charge-modifying agent is bonded to the membrane via the epoxide groups.

Convectively permeable adsorbents which permit fast contaminant depletion for a broad spectrum of contaminants and operating conditions, such as pH and salt concentration, are of great interest for biopharmaceutical purification processes.

Accordingly, it is therefore an object of the invention to provide membranes which, owing to their porous structure and their high mechanical and chemical stability, are suitable for use as base membranes for adsorption membranes having a high hydraulic permeability and binding capacity, and also to specify an inexpensive and environmentally friendly method for producing such flat adsorbents. Furthermore, it is a particular object of the present invention to provide membranes which permit, in comparison with the adsorbents known in the prior art, improved contaminant removal in a broad spectrum of operating conditions.

These objects are achieved by the subject matter characterized in the claims.

The adsorption membrane according to the invention comprises a cellulose hydrate matrix having pores which stretch from one main surface of the membrane to the other main surface of the membrane, wherein the membrane has functional groups (ligands) for adsorptive material separation on its inner and outer surfaces. Main surfaces shall be understood to mean the outer surfaces of a membrane.

A starting material used for the adsorption membrane according to the invention is a cellulose ester membrane which is contacted with at least one solution under conditions which lead firstly to swelling of the cellulose ester matrix and secondly, at the same time, i.e., in situ, to hydrolysis of the ester groups to hydroxyl groups, resulting in a cellulose hydrate membrane.

The swelling of the cellulose ester matrix during the hydrolysis of the ester groups is described by the degree of swelling, i.e., the ratio of the water permeability of the cellulose ester membrane wetted beforehand with water to the water permeability of the final, i.e., hydrolyzed, cellulose hydrate membrane, which has optionally been activatingly crosslinked and provided with ligand(s).

Subsequent to the hydrolysis, the cellulose hydrate matrix obtained is preferably crosslinked by reacting the hydroxyl groups with one or more at least bifunctional reagents, and functional groups (ligands) for enabling adsorptive material separation are then introduced into the crosslinked matrix.

Figure 4:
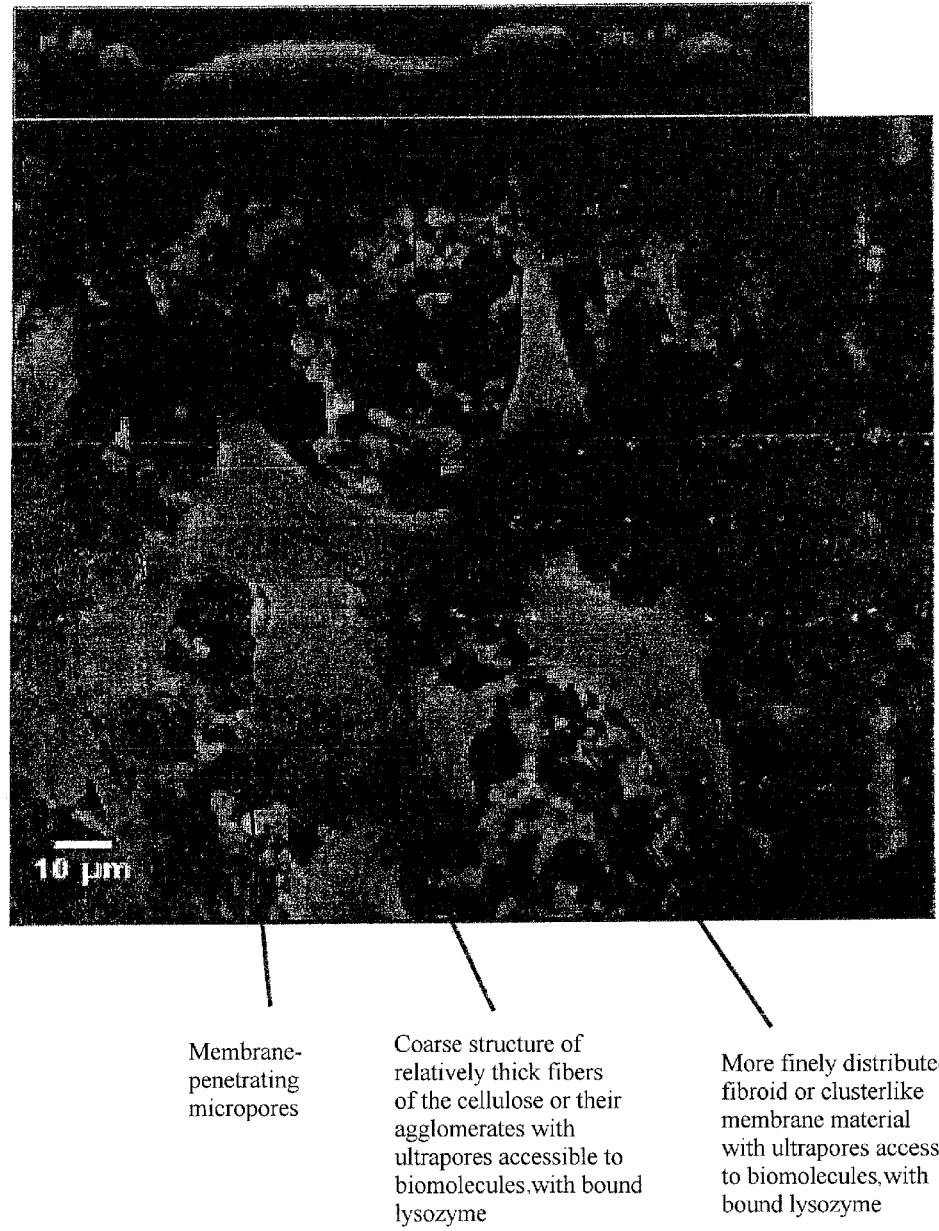

It was found that, surprisingly, the binding capacity of the cellulose hydrate membrane is distinctly increased when the hydrolysis step is carried out under conditions under which the cellulose can swell. The increase in the binding capacity for biomolecules may possibly be caused by the increased number of amorphous regions accessible to biomolecules in the cellulose. Swelling the cellulose support results in two types of pores: a) micropores having a diameter of >100 nm, which are generally smaller than the original pores of the cellulose ester membrane, and b) ultrapores (amorphous regions of the cellulose) having a diameter of <100 nm, which are shaped such that they are not accessible to Blue Dextran (available as Blue Dextran molecular weight 2 000 000 from Sigma, St. Louis, Mo., USA, product number D5751, CAS number: 87915-38-6) and which offer an additional adsorption surface accessible to ligands and adsorbates (cf. FIG. 1c). The effectiveness of adsorption of the membrane according to the invention is not restricted to the phase boundary of the connected micropores with the medium, but extends at least to a portion or even the entire volume in the ultrapores of the support (see FIG. 4). FIG. 4 shows a confocal micrograph image of a lysozyme-laden membrane according to the invention having ultrapores.

The swelling of the cellulose during the hydrolysis can be affected and controlled by a suitable pretreatment of the cellulose ester or by the parameters for hydrolysis (composition of the hydrolysis medium, type of additive, concentration of the additive, hydrolysis temperature). Thus, the permeability and binding capacity of the membrane can be adjusted. The adsorptive cellulose hydrate membranes produced in the method according to the invention show, compared to the cellulose hydrate membranes produced by production methods known in the field, distinctly higher binding capacities with comparable permeabilities.

As will be described hereinafter, the method for producing the membrane according to the invention can be carried out in three steps, wherein the setting of the desired degree of swelling, of the flow rate, and of the binding capacity can be controlled both by the parameters for the pretreatment (type of additive, concentration of the additive, pretreatment temperature) and the parameters for the hydrolysis (composition of the hydrolysis medium, type of additive, concentration of the additive, hydrolysis temperature). The membrane according to the invention can also be produced without pretreatment of the cellulose ester matrix. High degrees of swelling of the cellulose hydrate matrix can be achieved by the method according to the invention through a high concentration of alkali metal hydroxide in the hydrolysis medium, a high concentration of hydrogen-bond-breaking compounds, or a low temperature of the hydrolysis medium.

Through the type of crosslinking agent, the concentration of the crosslinking agent, the concentration of the crosslinking catalyst, the duration of crosslinking, optionally the type and concentration of an inert organic solvent and/or the crosslinking temperature, it is possible to control the degree of crosslinking, the pore size, and the number of residual active groups, e.g., epoxide groups. As a result, the activation often necessary for the bonding of the functional groups can take place as early as in the crosslinking step.

In a further step, functional groups can be bonded, for example, to the hydroxyl groups of the crosslinked membrane. Techniques for bonding functional groups are known per se to a person skilled in the art (e.g., from Greg T. Hermanson, A. Krishna Mallia, Paul K. Smith, Immobilized Affinity Ligand Techniques, Academic Press, INC, 1992).

Preferably, functional groups are bonded to the cellulose membrane via epoxide groups or aldehyde groups. The introduction of the epoxide groups can take place as early as in the crosslinking step or afterwards.

The combinations of the influencing factors (a) of the production conditions of the cellulose ester membrane used as a starting material, (b) of the conditions of any pretreatment carried out, (c) of the hydrolysis conditions, and (d) of the crosslinking conditions of the cellulose ester membrane also make it possible to produce multiple different end products from one starting membrane, resulting in a considerable simplification in terms of production technology.

Starting Membrane

The cellulose ester membrane used as a starting membrane in the method according to the invention has a pore size in the range from 0.1 to 20 μm, preferably from 0.5 to 15 μm, and more preferably from 1 to 10 μm, and is produced by a customary production method known in the field. To determine the pore size, a "capillary flow porometry test" is carried out. Further details can be found in the operating instructions (Capillary Flow Porometer 6.0, CAPWIN Software System, Porous Materials Inc.). Cellulose ester membranes can be composed of cellulose monoacetate, cellulose diacetate, cellulose triacetate, cellulose propionate, cellulose butyrate and cellulose acetobutyrate or other suitable cellulose esters, or cellulose nitrate, methylcellulose or ethylcellulose, and also mixtures thereof, preference being given to cellulose acetates, more particularly cellulose diacetate. It is known to a person skilled in the art that the cellulose ester membrane can, in part, also contain hydroxyl groups in addition to the ester groups.

Pretreatment

Before the hydrolysis, the cellulose ester membrane can be pretreated in a suitable medium. The temperature in the pretreatment step is preferably in a range from 20 to 100° C., particular preference being given to a temperature in a range from about 60° C. to about 80° C. A gas, such as, for example, air, an organic solvent, such as, for example, an alcohol, or an aqueous medium can be used as a pretreatment medium, preference being given to an aqueous medium. The pretreatment medium comprises preferably one or more additives which have a dissolving or plasticizing effect on a cellulose ester. Suitable additives are, in particular, acids, more particularly carboxylic acids, such as acetic acid, and water-soluble plasticizers for cellulose esters, such as diacetin, triacetin, and sulfolane. However, it is particularly preferred, in particular for commercial reasons, to use acetic acid as an additive for the pretreatment medium; although diacetin and triacetin also deliver excellent results, they are more expensive. The concentration of the additive in the pretreatment medium is not subject to any particular restrictions.

The duration of the pretreatment has no substantial influence on the pretreatment effect, provided that a minimum exposure time is applied which ensures a temperature equalization of the cellulose ester membrane in the pretreatment medium and a concentration equalization of any additive used in the membrane. The upper limit of the exposure time of the pretreatment medium is determined by the time from which a chemical reaction of the cellulose ester membrane with the pretreatment medium, for example by hydrolysis, could occur. In other words, the exposure time of the pretreatment medium is set such that no (premature) hydrolysis of the pretreated cellulose ester membrane occurs. Usually, the exposure time of the pretreatment medium to the cellulose ester starting membrane is between 0.1 second and 1 hour, preference being given to an exposure time in the range from 10 seconds to 10 minutes. The extent of the pretreatment effect is dependent on the highest temperature in conjunction with the highest concentration of the additive which affect the cellulose ester membrane. Thus, when the cooling or rinsing-out of the additive takes place over a longer period, this has no influence on the pretreatment effect already achieved. The pretreatment can therefore be terminated by rinsing the pretreatment additive out of the membrane and/or lowering the temperature of the pretreatment medium.

Hydrolysis

The optionally pretreated cellulose ester membrane is hydrolyzed with a suitable hydrolysis medium, whereby the cellulose hydrate membrane forms by swelling of the cellulose matrix. Depending on the type of pretreatment medium, the cellulose ester membrane can be used dry or wet in the hydrolysis step.

Through the swelling of the cellulose, the accessibility of the hydroxyl groups for the attachment of the functional groups and subsequently to the adsorbates is improved. The hydrolysis of the cellulose ester membrane is preferably carried out in an aqueous medium. More preferably, an aqueous hydrolysis medium having a pH of >7, i.e., a basic medium, is used. The hydrolysis medium comprises preferably an alkaline compound, preferably an alkali metal hydroxide. It is particularly preferred to use an aqueous solution of sodium hydroxide or lithium hydroxide. Use can also be made of mixtures of one alkali metal hydroxide and other alkaline compounds, such as alkali metal carbonate, such as sodium carbonate, potassium carbonate, cesium carbonate, sodium hydrogen carbonate, and/or sodium triphosphate, potassium triphosphate, sodium silicate and potassium silicate.

The concentration of the alkaline compound in the hydrolysis medium can be up to about 50% by weight, preference being given to a concentration in the range from 0.1 to 50% by weight and particular preference to a concentration in the range from 0.4 to 10% by weight. In a particularly preferred embodiment of the present invention, a hydrolysis medium composed of water and sodium hydroxide is used, the concentration of the sodium hydroxide in the hydrolysis medium being preferably in a range from 0.1 to 20% by weight, particularly preferably in a range from 0.4 to 4% by weight.

The hydrolysis medium can comprise one or more additives which have a swelling-influencing effect on a cellulose ester. Suitable additives are, in particular, salts, such as sodium chloride, sodium sulfate, and sodium acetate, hydrogen-bond-breaking compounds, such as urea, or organic solvents, such as ethylamine. The organic solvent is preferably selected from the group consisting of alcohols, ketones, and ethers. Particularly preferred solvents are ethanol, methanol, ethylene glycol, propylene glycol, glycerol, acetone, dioxane, or diglyme. The additive in the hydrolysis medium should influence the swelling, but not completely suppress it.

The temperature of the medium used in the hydrolysis step can be in the range from about 10° C. up to the boiling point of the hydrolysis medium, preference being given to a temperature in a range from 15° C. to about 25° C.

The duration of hydrolysis is determined by the composition of the hydrolysis medium and the hydrolysis temperature. Usually, the duration of hydrolysis is in the range from 0.1 to 60 minutes, preference being given to a duration of hydrolysis in the range from 5 to 45 minutes. A particularly preferred duration of hydrolysis in the range from 20 to 40 minutes.

The cellulose hydrate membrane obtained can have any suitable thickness. Preferably, the layer thickness is in the range from 50 to 500 μm, more preferably in the range from 100 to 300 μm. The cellulose hydrate membrane obtained can be flat or else cylindrical. Cylindrical membranes are referred to as hollow fiber membranes, capillary membranes, or tubular membranes.

Crosslinking

In a further preferred embodiment, the cellulose hydrate membrane obtained following any pretreatment carried out and following the hydrolysis with swelling is crosslinked with a crosslinking agent to increase the chemical resistance of the membrane and/or to introduce functional groups.

The crosslinking agent has at least two functional groups in the molecule which are reactive with the hydroxyl groups of cellulose and thus make crosslinking of cellulose possible. The usable crosslinking agents are, in principle, not subject to any particular restrictions and a person skilled in the art is capable of selecting them from a series of crosslinking agents usable for the crosslinking of cellulose. However, it is preferred to use, in the crosslinking step, a diepoxide compound or else other compounds which are reactive with hydroxyl groups of cellulose and have at least two reactive functional groups, such as diisocyanate, epichlorohydrin, epibromohydrin, dimethylurea, dimethylethyleneurea, dimethylchloro-silane, bis(2-hydroxyethyl)sulfone, divinyl sulfone, alkylene dihalogen, hydroxyalkylene dihalogen, and glycidyl ethers.

From the group of the glycidyl ethers, preference is given to 1,4-butanediol diglycidyl ether, ethylene glycol diglycidyl ether, glycerol diglycidyl ether, and polyethylene glycol diglycidyl ether.

Particular preference is given to the use of 1,4-butanediol diglycidyl ether or epichlorohydrin as a crosslinking agent.

Optionally, a mixture of different crosslinking agents can be used.

The crosslinking can take place in an aqueous medium, in an organic solvent, or else in a mixture of water and an organic solvent. Preferably, the crosslinking is carried out in an aqueous medium.

It is further preferred to use a crosslinking catalyst, such as sodium hydroxide, to accelerate the crosslinking of cellulose with the crosslinking agent.

The temperature of the medium used in the crosslinking step can be in the range from about 4° C. up to the boiling point of the crosslinking medium, preference being given to a temperature in a range from 5° C. to about 70° C. A particularly preferred temperature is in the range from 20° C. to 40° C.

Usually, the duration of crosslinking is in the range from 10 minutes to 100 hours, preference being given to a duration of crosslinking in the range from 30 minutes to 48 hours. A particularly preferred duration of hydrolysis is in the range from 2 to 24 hours.

As described above, the method for producing the membrane according to the invention can be carried out in three steps, wherein the setting of the desired degree of swelling of the matrix can be controlled both by the parameters for the pretreatment (type of additive, concentration of the additive, pretreatment temperature) and the parameters for the hydrolysis (composition of the hydrolysis medium, type of additive, concentration of the additive, hydrolysis temperature). The membrane according to the invention can also be produced without pretreatment.

Activation and Bonding of Functional Groups

In a further step, functional groups can be bonded to the hydroxyl groups of the crosslinked cellulose hydrate membrane. Techniques for bonding functional groups are known to a person skilled in the art (e.g., from Greg T. Hermanson, A. Krishna Mallia, Paul K. Smith, Immobilized Affinity Ligand Techniques, Academic Press, INC, 1992). Grafting methods for functional monomers or polymers and polymer coating methods are known to a person skilled in the art and can be used to introduce functional groups.

Preferably, functional groups are bonded to the cellulose membrane via epoxide groups or aldehyde groups. The epoxide activation can take place as early as in the crosslinking step or afterwards.

It is also possible to introduce functional groups during the crosslinking, e.g., by adding an amine and/or a monofunctional epoxide compound, such as phenyl glycidyl ether or butyl glycidyl ether, to a diepoxide compound.

Preferably, the functional groups can be a constituent of an oligomeric or polymeric spacer which links the functional groups to the cellulose membrane.

Particularly preferably, the functional groups are ligands which preferably comprise anionic or cationic groups. The anionic groups can, for example, be sulfonic acid, phosphoric acid, or carboxylic acids, and the cationic groups can be primary, secondary, tertiary, and/or quaternary amines.

It is more particularly preferred that the cationic groups are primary, secondary, and/or tertiary amines, wherein the primary, secondary, and/or tertiary amines can be monomeric or polymeric amines. The primary, secondary, and/or tertiary amines are preferably polymeric compounds having linear and/or branched and/or cyclic structures. Within the present invention, polymeric amines are understood to mean polyamines having at least one primary, secondary, and/or tertiary amine group in a polymer chain.

Polymers which have a linear, branched, or cyclic structure and which contain primary, secondary, and/or tertiary amine groups are highly suitable for covalent immobilization on activated surfaces. Such polymers offer a sufficient number of cationic groups which are capable of adsorbing negatively charged substances. The direct covalent attachment of polymeric amines to porous supports leads to stable positively charged surfaces. Polyamines are multifunctional polymers which are providable with cationic charges and which have a branched, spheric structure. Owing to their high charge density, these polymers strongly adsorb to negatively charged surfaces, such as cellulose, polyester, polyolefins, polyamides, and metals. They are therefore used, inter alia, for mediating improved adhesion between different materials.

By using polymeric amines as ligands, it is possible to provide a membrane which, in comparison with the absorbents known in the prior art, exhibit improved contaminant removal with a broad spectrum of operating conditions. The contaminants can be any materials whose absence or removal from a fluid is required or desirable for technical, regulatory, or other reasons. Preferably, the contaminants are viruses, proteins, amino acids, nucleic acids, endotoxins, protein aggregates, ligands, or parts thereof. More particularly, the cellulose hydrate membrane according to the invention in conjunction with a polyamine functionalization is suitable for contaminant removal when high binding capacities for proteins are required.

All suitable polymeric amines can be used. However, preference is given to polymeric amines which contain mainly primary amine groups. Particular preference is given to polymeric amines which contain mainly primary amine groups and have a molecular weight of more than 500 g/mol.

In a particularly preferred embodiment of the present invention, the polymeric compounds are selected from the group consisting of the polyalkyleneimines having a molar mass in the range from 800 to 1 000 000 g/mol. Preferably, the polyalkyleneimine is a polyethyleneimine. Polyethyleneimines (PEI) precipitate nucleic acids and proteins out of aqueous media. PEI immobilized on porous supports effectively filters, for example, endotoxins and pathogens out of blood plasma.

In another particularly preferred embodiment, the polymeric compounds are selected from the group consisting of the polyallylamines having a molar mass in the range from 3000 to 150 000 g/mol.

In a further preferred embodiment, the polymeric compounds are selected from the group consisting of the polyvinylamines having a molar mass in the range from 5000 to 500 000 g/mol. Polyvinylamine has the highest cationic charge density known to date. At higher degrees of hydrolysis, the charge density decreases with increasing pH. In contrast to other polymers, polyvinylamine has, however, a significant charge density which is constant at ~6 meq/g even at high pH (pH=9–10). At degrees of hydrolysis below 50%, the charge density is not affected by the pH.

Figure 6:
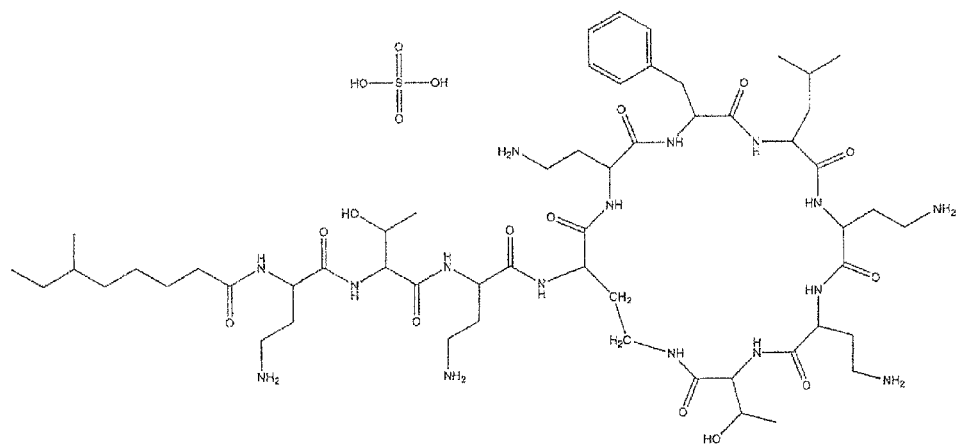

In a further preferred embodiment, the polymeric compound is polymyxin B (cf. FIG. 6). Polymyxin B is a cyclic peptide which has a fatty acid residue and which has cationic amine groups at a physiological pH and has hydrophilic and hydrophobic properties.

The polymeric amines can either be bonded directly to the surface of the support or via a spacer to the support, or be bonded via an epoxy groupcomprising polymer layer on the surface of the support, such as, for example, by polymer-analogous reaction of glycidyl methacrylate-grafted (GyIMA-grafted) supports with the polyamines.

"Polymer-analogous reactions" shall be understood here to mean reactions of macromolecules in which the chemical composition and thus also the properties of a polymer are changed while preserving the degree of polymerization.

Techniques for immobilizing functional groups via amino groups are known to a person skilled in the art (Greg T. Hermanson, A. Krishna Mallia, Paul K. Smith, Immobilized Affinity Ligand Techniques, Academic Press, INC, 1992). Preference is given to using, for example, aldehyde- or epoxyactivated supports which can be reacted with amines. Active groups can, as described above, be introduced in the production of the porous support.

In a preferred embodiment of the present invention, a diepoxide or triepoxide compound can be added to the polymeric amine before or during the reaction with the membrane. The epoxide compound leads to crosslinking of the polymeric amine and to covalent bonding of the polyamine to the support surface. Additives, such as salts, polymers, or organic solvents, can be added to the polyamine and/or to the support before or during the reaction of the polyamine with the support surface.

The polymeric amines are preferably reacted in aqueous solutions with the activated supports. The concentration can be varied as desired.

However, it was established that a reaction of, for example, glycidyl methacrylate-grafted (GyIMA-grafted) polymer layers with a polymeric amine leads to crosslinking of the polymer layer. A multiple-point-attachment reaction of the polymeric amine in the GyIMA-polymer layer can take place either intramolecularly with neighboring glycidyl groups of the same polymer chain or intermolecularly with glycidyl groups of two polymer chains. The second possibility leads to crosslinking of the polymer layer on the membrane. The crosslinking causes the polyamine layer to be no longer accessible to biomolecules, this becoming apparent with low binding capacities for proteins (see comparative example 2). This technique is therefore not suitable for immobilizing polymeric amines of a higher molecular weight.

In a further preferred embodiment of the present invention, at least one primary, secondary, or tertiary amine group of the polymeric amine is reacted with a component selected from the group comprising phenyl glycidyl ether, 1,2-epoxyethylbenzene, dodecyl glycidyl ether, tetradecyl glycidyl ether, benzyl chloride, (3-glycidyloxypropyl)trimethoxysilane, bis[(4-glycidyloxy)phenyl]methane, bisphenol A diglycidyl ether, 1,4-butanediol diglycidyl ether, 6-hexanediol diglycidyl ether, N,N-diglycidyl-4-glycidyloxyaniline, 4,4'-methylenebis(N,N-diglycidylaniline), and/or tris(4-hydroxyphenyl)methane triglycidyl ether. In this way, it is possible to control the affinity of the adsorbent for the target adsorbates. The free primary, secondary, or tertiary groups of the polymeric amine can be reacted with the further functional groups during or after the reaction with the porous support.

In all embodiments in which at least one polymeric amine is bonded as a ligand to the membranes according to the invention, this polymeric amine is directly immobilized on the surface of the support, i.e., without an intermediate grafting chain.

The structure of the membrane according to the invention permits a direct surface attachment of polymeric amines (without additional, intermediate grafting chains) for the formation of a polyamine layer accessible to biomolecules on the membrane surface.

An advantage of the membrane according to the invention is that it is possible to produce optimal adsorbents for the desired application through the large selection of monomeric or polymeric amines and of hydrophobic functional groups of the abovementioned compounds usable for the reaction with the polymeric amines.

In a further preferred embodiment of the present invention, the ligands are affinity ligands, e.g., p-aminobenzamidine, biomimetic ligands, and/or proteins.

In a further preferred embodiment of the present invention, the ligands are selected from the group consisting of the metal chelates.

In a further preferred embodiment of the present invention, the ligands are hydrophobic and are selected from the group consisting of the $C_1$-$C_{20}$-alkyl groups, $C_6$-$C_{25}$-aryl groups, $C_7$-$C_{25}$-arylalkyl groups and their derivatives and/or —$[(CH_2)_m$—$O$—$]_n$—$R$, where m is 2 or 3, n is a whole number greater than 1, and R is —H or —$C_1$-$C_5$-alkyl.

In a further preferred embodiment of the present invention, the ligands are selected from the group consisting of the reactive epoxide, aldehyde, azlactone, N-hydroxysuccinimide, and/or carbodiimide groups.

Finally, the at least one ligand can be a catalyst in a further preferred embodiment of the present invention.

The at least one ligand can preferably be bonded indirectly to the cellulose membrane via an oligomeric or polymeric spacer or can particularly preferably be bonded directly to the cellulose membrane.

Preferably, at least two structurally different ligands are bonded to the membrane according to the invention.

The membranes according to the invention can, after the introduction of functional groups, optionally be dried. Membranes can be directly dried to remove water or organic solvents, preferably alcohol, or can be dried after carrying out a stepwise replacement of water with an organic solvent. Preferably, the membranes are dried to remove a medium which comprises a pore-stabilizing compound. Particularly preferably, the membranes according to the invention are dried to remove an aqueous glycerol solution. The concentration of the glycerol is preferably in the range from 5 to 40% per weight, based on the aqueous solution.

Explanation of the Examples

Crosslinked cellulose hydrate membranes having a low degree of swelling are, for example, produced from cellulose ester membranes hydrolyzed with ethanolic potassium hydroxide solution. A cellulose acetate membrane yields, in this way, a cellulose hydrate membrane which has a negligibly lower flow rate (see example 1), but which has, after introduction of ligands, virtually no adsorption capacity (binding capacity) (see table 2).

It has now been found that, although hydrolysis with an aqueous sodium hydroxide solution lowers the flow rate (see example 2), distinctly increased binding capacities occur following overlaying with various ligands, increasing sodium hydroxide solution concentrations resulting in a stronger flow rate reduction and higher binding capacities (see table 2). Compared with the membrane-penetrating micropores which mainly form in the hydrolysis with ethanolic potassium hydroxide solution, the formation of a multiplicity of small ultrapores seems to be preferred in the hydrolysis with aqueous sodium hydroxide solution. A higher hydrolysis temperature and also an additional content of electrolytes, including sodium acetate already formed in the hydrolysis, have the same effect as a lower sodium hydroxide solution concentration.

WO 2007/017085 A2 describes a method for producing crosslinked cellulose hydrate membranes which consists in the simultaneous hydrolysis and crosslinking of cellulose ester membranes and is intended to be equally suitable for filtration and adsorption membranes. One of the goals of the invention described therein is the hydrolysis and crosslinking of the cellulose ester under conditions which do not affect the structure and permeability of the membrane. Through simultaneous hydrolysis and crosslinking under conditions which suppress swelling and structural change ($Na_2SO_4$, low sodium hydroxide solution concentration), no significant binding capacity is found (see comparative example 1). Only when the alkaline solution concentration is increased is there an increase in the binding capacity. However, the swelling of the cellulose also leads here to a change in the pore structure, contrary to the simultaneous hydrolysis and crosslinking process described in the prior art. The binding capacity here is, however, only about 5% of the binding capacity in comparison with the hydrolysis and crosslinking carried out separately under swelling conditions (see example 2 and comparative example 1).

Furthermore, it has been found that different pretreatment of the cellulose acetate membrane has different effects on the properties of the adsorptive membrane according to the invention. The flow rate decreases and the binding capacity increases when the cellulose acetate membrane has been heated to 80° C. under air prior to the hydrolysis (see example 3). When the cellulose acetate membrane is heated to 80° C. in 20% acetic acid prior to the hydrolysis (see example 4), the flow rate increases in comparison with the non-pretreated membrane from example 2 and the binding capacity changes depending on the size of the protein. The binding capacity increases for lysozyme (14.3 kDa); the binding capacity decreases for bovine serum albumin (BSA; 60 kDa) and gamma-globulin (150 kDa). The pretreatment can, for example, be advantageous in specific separation tasks when solely the specificity of the ligand is not sufficient for material separation, and the molar masses of the components to be separated are so different that the overall result of superimposing a size exclusion effect on purely adsorptive material separation is an improvement in the separation capacity, and the influencing of the pore size of the ultrapores through choice of base and its concentration needs support. A complete separation solely on the basis of this effect is, however, not possible because the size exclusion only becomes effective for the adsorption on the inner surface of the ultrapores, but not on the outer surface of the micropores.

These findings indicate, in the case of hydrolysis and crosslinking of cellulose acetates, complex swelling and deswelling procedures whose effects with regard to the structure of the end product are difficult to summarize because there are both procedures in which a flow rate reduction is coupled with an increase in the binding capacity and procedures in which this is not the case. The former are referred to hereinafter as "productive", the others as "unproductive". The pretreatment of the cellulose acetate membrane has different effects on the change in pore structure, and the form ation of micropores and also of ultrapores. It is thus possible, through a suitable choice of the pretreatment, to influence the flow rate, the binding capacity but also the size exclusion of the ultrapores of the adsorptive membrave according to the invention. The main goal of the method according to the invention is the restriction to productive flow rate reductions, which should take account not only of the swelling behavior of the starting material, the cellulose acetate membrane, and the end product, the crosslinked cellulose hydrate membrane, but also the entire spectrum of the intermediate products in the partially hydrolyzed and partially crosslinked state. For example, it is known that cellulose acetates of decreasing acetyl content even pass through, in a narrow range, a state of water solubility.

According to the invention, a cellulose ester membrane is sequentially hydrolyzed in a swelling medium, preferably an aqueous solution of an alkali metal hydroxide, optionally crosslinked with an at least bifunctional agent and provided with an adsorption-effective ligand. The swelling capacity of the alkali metal hydroxides increases with smaller cation radii and higher concentrations (see example 5).

The cellulose is preferably crosslinked according to the invention with 1,4-butanediol diglycidyl ether. In an embodiment of the invention, the cellulose is crosslinked with 1,4-butanediol diglycidyl ether such that, because of a partly one-sided reaction, a sufficient number of unreacted epoxide groups are preserved ("activating crosslinking", see example 2) and can serve to bond or to couple or to construct ligands. The unreacted epoxide groups are relatively hydrolysis-stable and were used for subsequent reactions even after humid storage at room temperature for up to 24 hours. In another embodiment of the invention for bonding "active" ligands, the crosslinking is carried out under more severe conditions (longer duration of crosslinking and/or higher alkali concentration and/or higher temperature) so that, with increased reaction with the cellulose and/or increased hydrolysis of the surplus groups, virtually no epoxide groups remain ("nonactivating crosslinking", see example 6). Remaining epoxide groups can also be hydrolyzed by subsequent treatment with, for example, 5% sulfuric acid at elevated temperature.

The flow rate of the membrane according to the invention in example 2 for a 20 mM Tris/HCl buffer with a pH of 7.3 is 8% greater than that for pure water. Corresponding values for adsorption membranes which were produced by coating according to the prior art are in the range from 20%, in the case of a crosslinked auxiliary polymer, to 200%, in the case of an uncrosslinked auxiliary polymer. The resulting pore structure, by virtue of the low dependence of the flow rate on the ionic strength of the medium, appears to be a hybrid of aerogel and xerogel, similar to a crosslinked agarose gel.

It is difficult to distinguish the adsorption membranes according to the invention from adsorption membranes produced by polymer coating or grafting according to the prior art by scanning electron microscopy because its resolution would be overwhelmed by the small-pored structures (i.e., ultrapores) which constitute the main difference. In contrast, the characterization of adsorptive membranes by means of confocal laser scanning microscopy (CLSM) simultaneously delivers, under suitable conditions, information both about the pore structure and about the distribution of protein bound to functional groups in the membrane. For this purpose, the membrane material and protein must be labeled with two different fluorescent dyes. All microscopic measurements were carried out at approximately the same distance (about 20 μm) from the respective outer surface. In all cases, three independent measurements at different x,y-positions led to very similar results characteristic of the respective membrane type.

Characteristic of all membrane samples is a very coarse structure (dark areas in FIGS. 2-4) composed of relatively thick fibers or their agglomerates interspersed with more finely distributed fibroid or clusterlike membrane material with completely or partially undyed areas which can be attributed to the membrane-penetrating micropores with dimensions of up to about 20 μm. The protein distribution was clearly identifiable for all membrane samples. However, very great differences with regard to protein amount (fluorescence intensity, bright areas) and protein distribution in the pore structure (dark areas) were found. The total fluorescence intensities were distinctly different; for the membrane according to the invention in example 2, it was even necessary to select a lower amplification than for the other membranes:

Membrane from example 2>Sartobind® S membrane>>Membrane from example 1

These results correlate well with the figures for the binding capacity:

Membrane according to example 1: 0.01 mg/cm$^2$
Sartobind® S membrane: 0.90 mg/cm$^2$
Membrane according to example 2: 2.06 mg/cm$^2$ Using the investigative technique, it was possible to identify clear and great differences with regard to protein binding between the established Sartobind® S membrane (FIG. 2) and the membranes functionalized with sulfonic acid ligands from example 1 (FIG. 3) and example 2 (FIG. 4). With the membranes from examples 1 and 2, the fluorescence intensities for the protein (bright areas) correlate with the nominal protein-binding capacities, i.e., the membrane from example 1 exhibits only a very low binding capacity, while the membrane according to the invention from example 2 exhibits a distinctly higher binding capacity.

Based on the same pore structure of the base support, the protein in the Sartobind® S membranes binds, in particular, in the volume of the micropores, a three-dimensional functional layer being essential for the protein binding. These membranes show, at the edges of the pores, sharp boundaries between the material of the membrane (dark areas) and the protein layer (bright areas). Because of the restricted range of this functional layer, small fractions of the pore volume remain in which no protein is bound. In the case of the membrane from example 1, the binding takes place directly on the membrane material, recognizable by small, bright points in FIG. 2. In contrast to this, in the case of the membrane according to the invention from example 2, clearly very large amounts of protein are bound in the ultrapores of the coarse fiber structure and also in the more finely distributed fibroid or clusterlike membrane material. Between the distributions of cellulose and protein, a very good correlation is found, also recognizable visually from the fact that only the mixed color of the dyes used is recognizable in the overlay, because both pore surface and protein are visible in the depth of the ultrapores. By far the largest fraction of the volume of the micropores contains no protein.

In order to quantify the ultrapores of the membranes according to the invention, an experiment was carried out in which the accessibility of the pores to Blue Dextran was determined. The experiment was carried out in the manner described in example 14. The result of the evaluation is shown in table 1 and in FIG. 5.

Figure 5:
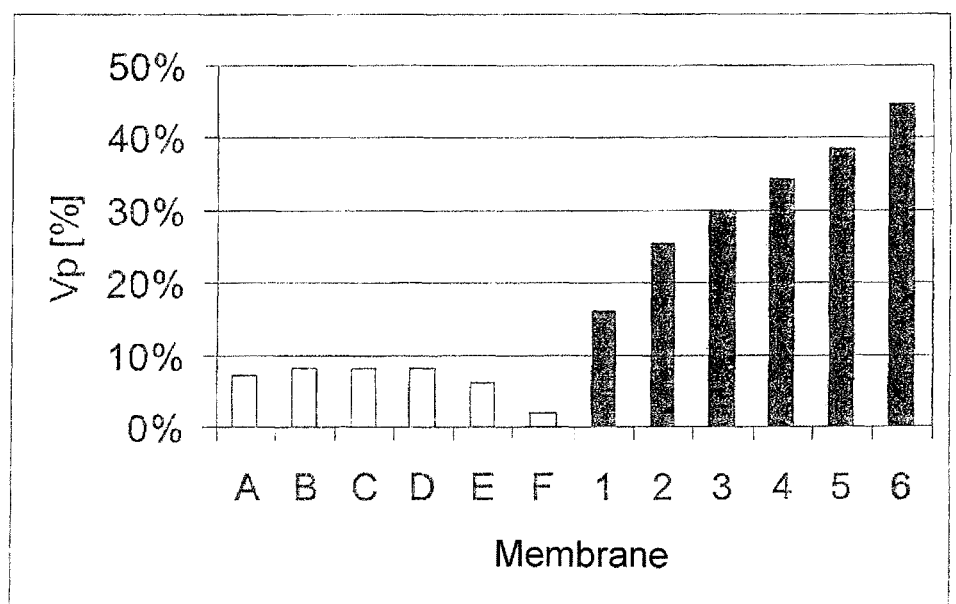

In FIG. 5, a distinct difference is recognizable between the ultrapores inaccessible to Blue Dextran for the membranes A-F known in the prior art and membranes according to the invention from example 14. In the case of the membranes according to the invention, which were hydrolyzed under swelling conditions, more than 15% of the entire pore volume is in the range of ultrapores (i.e., pores having a diameter <100 nm which are not accessible to Blue Dextran), whereas it is less than 8% for the comparative membranes A-F.

Accordingly, membranes according to the invention have a volume of ultrapores which are accessible to water, but not to Blue Dextran having a molecular weight Mw of 2 000 000, of more than 15%, preferably more than 18%, more preferably more than 20%, even more preferably more than 25%, and most preferably more than 30% of the entire pore volume.

Figure 7:
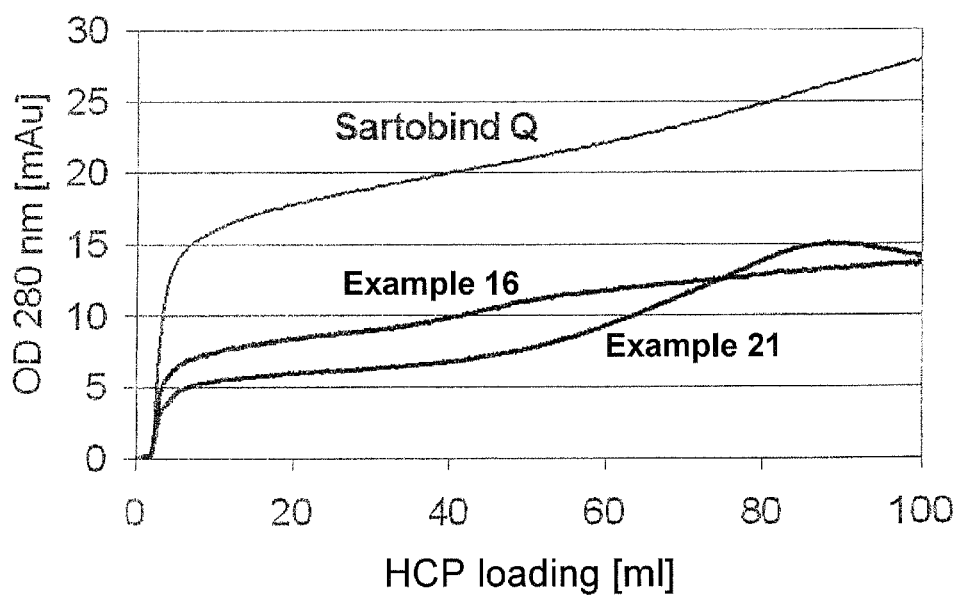

Furthermore, it has been found that, with the introduction of a polyamine functionalization into the membranes according to the invention, the membranes show, in comparison with the Sartobind® Q membrane from the prior art, comparable or higher binding capacities for the model protein bovine serum albumin (BSA), distinctly higher charge densities, and distinctly higher dynamic binding capacities for DNA as model contaminants (cf. examples 15 to 23 and also comparative examples 3 and 4). FIG. 7 shows breakthrough curves for a model HCP mixture. The breakthrough curves show that the membranes according to the invention from examples 16 and 21 have distinctly higher affinities for the host cell proteins, since the fraction of the bound proteins, which corresponds to the area above the breakthrough curve, is greater than for the Sartobind® Q membrane. Since the HCP mixture is a mixture of proteins of varying size and isoelectric points (i.e., charge) (cf. "Evaluation of the membranes (for examples 15 to 23 and comparative examples 3 and 4)", paragraph 5), the shift of the breakthrough downward (increase in the area above the breakthrough curve) with respect to the Sartobind® Q membrane means that multiple different proteins bind in a larger amount to the membranes according to the invention. This is in agreement with the goal of the invention.

The bacteriophage ΦX174 having a diameter of about 30 nm and an isoelectric point pI of 6.4-6.7 is used as a model virus for investigating the efficiency of virus depletion. Its depletion with the membranes according to the invention at different salt concentrations in a buffer in comparison with the Sartobind® Q membrane known in the prior art is investigated ("6) Binding of model viruses"). The results in table 4 show that the membranes according to the invention effectively deplete the phage at high salt concentrations, whereas the depletion with the Sartobind® Q membrane is only possible at low salt concentrations. This is in agreement with the object of the present invention to provide membranes which permit, in comparison with the adsorbents known in the prior art, improved contaminant removal in a broad spectrum of operating conditions.

FIGURES

FIG. 1a): Schematic illustration of the binding of protein to micropores of an adsorptive membrane known in the prior art and produced as in example 1.

FIG. 1b): Schematic illustration of the binding of protein to an adsorptively active polymer coating of adsorptive membranes as described in the prior art which consist of one or more support structures and one or more adsorptively active polymer coatings.

FIG. 1c): Schematic illustration of the binding of protein in the ultrapores of an adsorptive membrane according to the invention.

Figure 2:
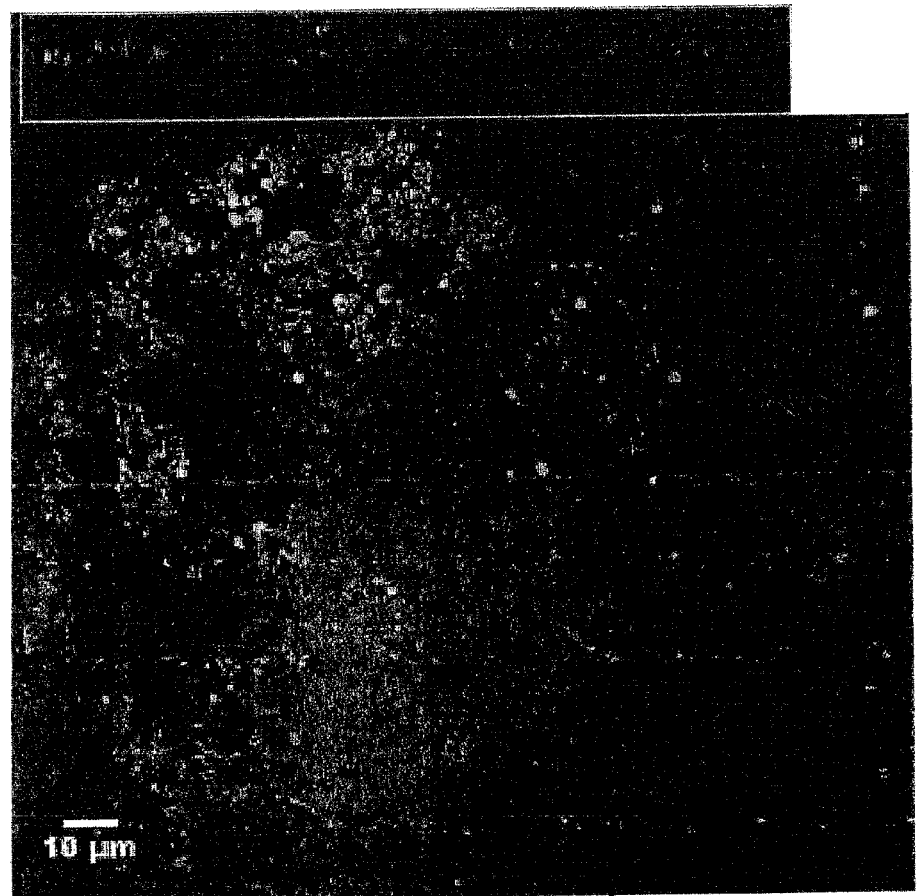

FIG. 2: CLSM image of the pore morphology and protein distribution on the upper side of the Sartobind® S membrane following labeling of the cellulose with fluorescent dye and loading with fluorescently labeled lysozyme.

Figure 3:
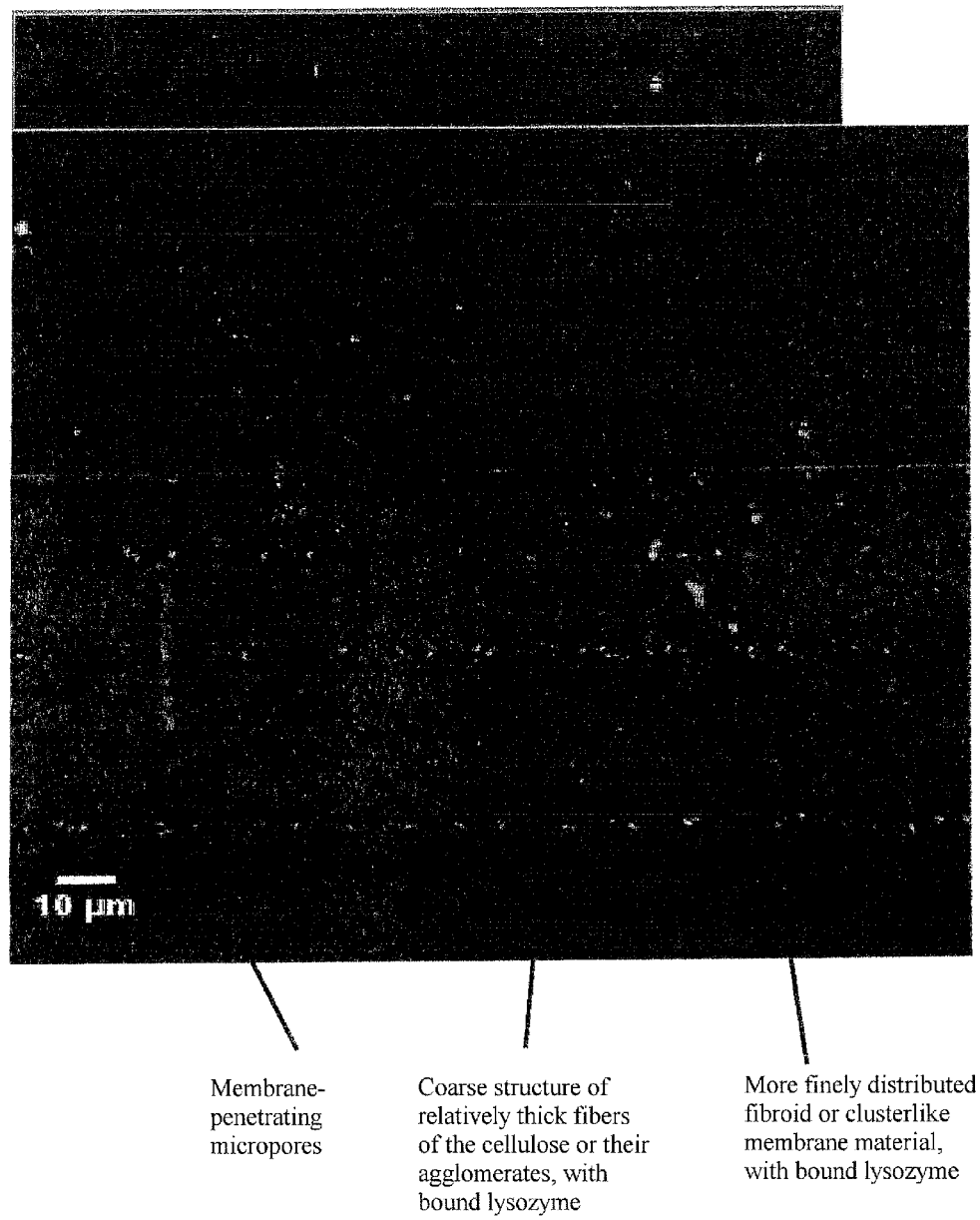

FIG. 3: CLSM image of the pore morphology and protein distribution on the upper side of the membrane reacted with sulfonic acid ligands according to example 1 following labeling of the cellulose with fluorescent dye and loading with fluorescently labeled lysozyme.

FIG. 4: CLSM image of the pore morphology and protein distribution on the upper side of the membrane reacted with sulfonic acid ligands according to example 2 following labeling of the cellulose with fluorescent dye and loading with fluorescently labeled lysozyme.

FIG. 5: Comparison of the percentage of pores inaccessible to Blue Dextran having a molecular weight Mw of 2 000 000 in the membranes:
A: Membranes from example 1
B-F: Cellulose membranes according to the prior art 0.2-0.45 µm from Sartorius Stedim Biotech GmbH
1-6: Membranes according to the invention from example 14

FIG. 6: Structure of polymyxin B

FIG. 7: Breakthrough curves for a model HCP mixture for the Sartobind® Q membrane and for the membranes according to the invention of examples 16 and 21.

EXAMPLES

All mention in the examples of a CA membrane refers to a polyesternonwoven-reinforced type of cellulose acetate membrane having a pore diameter of about 3 µm (measured with a Coulter Capillary Flow Porometer 6.0, CAPWIN Software System, Porous Materials Inc.), which has a water flow rate of 730 ml/(min×bar×cm$^2$). The thickness of the modified membrane samples was, on average, 250 µm. All flow rate figures are in ml/(min×bar×cm$^2$), and all binding capacity figures are in mg/cm$^2$. Unless stated otherwise, percentages are based on weight. For examples 15 to 23 and comparative examples 3 and 4, the membranes have a water flow rate in the range from 600 to 700 ml/(min×bar×cm$^2$).

Example 1

Activatingly Crosslinked Cellulose Hydrate Membrane Having a Low Degree of Swelling for Comparative Examples The membrane was produced in the following way: A CA membrane, as mentioned above, was used as starting material. This CA membrane was hydrolyzed for three minutes at room temperature with a 15% potassium hydroxide solution in 80% ethanol. Subsequently, it was rinsed for three minutes with a 6.8% acetic acid solution, twice with ethanol, and then for 15 minutes with running reverse-osmosis (RO) water. Afterwards, the membrane was dried for 20 minutes at 80° C. in a circulating air drying cabinet.

In the next step, the dried membrane thus obtained was treated for 30 minutes at room temperature with 30% 1,4-butanediol diglycidyl ether in an aqueous 0.1 M sodium hydroxide solution and aqueous 0.1% sodium borohydride solution, and then the moist membrane was left to stand for 20 hours in a closed vessel at room temperature.

Finally, the membrane was rinsed for 30 minutes with running water.

The water flow rate of the activatingly crosslinked cellulose hydrate membrane thus produced was 630 ml/(min×bar×cm$^2$). The degree of swelling was 1.16.

Example 2

Activatingly Crosslinked Intermediate Product for an Adsorption Membrane According to the Invention A CA membrane, as in example 1, was used as starting material. This CA membrane was hydrolyzed for 30 minutes at room temperature with a 0.6 M aqueous sodium hydroxide solution (i.e., under swelling conditions) and subsequently rinsed for 3×10 minutes with a 0.5 M aqueous sodium hydroxide solution. The membrane obtained was treated (i.e., crosslinked) for 30 minutes at room temperature with 30% 1,4-butanediol diglycidyl ether in a 0.1 M aqueous sodium hydroxide solution and 0.1% aqueous sodium borohydride solution, and then the moist membrane was left to stand for 20 hours in a closed vessel at room temperature.

Finally, it was rinsed for 30 minutes with running water.

The water flow rate of the activatingly crosslinked intermediate product was 45 ml/(min×bar×cm$^2$), and the degree of swelling was 16.2.

Example 3

Activatingly Crosslinked Intermediate Product for an Adsorption Membrane According to the Invention: Pretreatment of the CA Membrane A CA membrane was treated in the same way as in example 2, with the exception that the CA membrane was heated for 20 minutes at 80° C. in the drying cabinet prior to the hydrolysis.

The water flow rate of the resulting activatingly crosslinked intermediate product was 21 ml/(min×bar×cm$^2$), and the degree of swelling was 34.8.

Example 4

Activatingly Crosslinked Intermediate Product for an Adsorption Membrane According to the Invention: Pretreatment of the CA Membrane A CA membrane was treated in the same way as in example 2, with the exception that the CA membrane, prior to the hydrolysis, was heated in a 20% acetic acid solution to 80° C. and rinsed for 15 minutes with running water.

The water flow rate of the resulting activatingly crosslinked intermediate product was 180 ml/(min×bar×cm$^2$), and the degree of swelling was 4.06.

Example 5

Various Alkali Hydroxides

CA membranes were, in each case, hydrolyzed in 0.5 M aqueous solutions of LiOH, NaOH, and KOH for 30 minutes at room temperature, and subsequently, without rinsing, crosslinked for 3.5 hours at room temperature with aqueous solutions of 15% 1,4-butanediol diglycidyl ether and 0.1% sodium borohydride solution in the same alkali metal hydroxide solutions. The membranes were further reacted with a quaternary ammonium ligand by treating the crosslinked membranes for 35 minutes at 30° C. in a 10% aqueous solution of trimethylamine and for 5 minutes at room temperature in 5% sulfuric acid solution and then rinsing them for 10 minutes with running water. The results are reported in table 2.

Example 6

Nonactivatingly Crosslinked Intermediate Product for Adsorption Membrane According to the Invention A CA membrane, as in example 1, was used as a starting membrane. This CA membrane was hydrolyzed for 30 minutes at room temperature with a 0.6 M aqueous sodium hydroxide solution and subsequently rinsed for 3×10 minutes with a 0.5 M aqueous sodium hydroxide solution. The membrane obtained was treated (crosslinked) for 30 minutes at room temperature with aqueous 15% 1,4-butanediol diglycidyl ether in a 0.5 M aqueous sodium hydroxide solution and 0.1% aqueous sodium borohydride solution, and then the moist membrane was left to stand for 20 hours in a closed vessel at room temperature. Finally, it was rinsed for 30 minutes with running water.

The water flow rate of the nonactivatingly crosslinked intermediate product was 31 ml/(min×bar×cm$^2$), and the degree of swelling was 23.5.

Example 7

Introduction of Quaternary Ammonium Ligands (Q Membrane)

Activatingly crosslinked membranes (intermediate products) were treated for 35 minutes at 30° C. in a 10% aqueous solution of trimethylamine and for 5 minutes at room temperature in a 5% sulfuric acid solution and then rinsed for 10 minutes with running water, to obtain membranes having quaternary ammonium ligands (hereinafter: Q membranes).

Example 8

Introduction of Sulfonic Acid Ligands (S Membrane)

Activatingly crosslinked membranes (intermediate products) were treated for 45 minutes at 80° C. in an aqueous solution of 30% sodium sulfite and 2.5% Na$_2$HPO$_4$×H$_2$O at a pH of 8.0 and then rinsed for 10 minutes with running water, for 5 minutes with 35 g of a 1% HCl solution, for 2×5 minutes with 30 g each time of an aqueous 1 M NaCl solution, for 5 minutes with 500 g of a 5% H$_2$SO$_4$ solution, and for 10 minutes with running water, to obtain membranes having sulfonic acid ligands (S membranes).

Example 9

Introduction of Iminodiacetic Acid Ligands (IDA Membrane)

Activatingly crosslinked membranes (intermediate products) were treated for 45 minutes at 80° C. with a 13% aqueous solution of iminodiacetic acid at a pH of 11.2 and then rinsed for 10 minutes with running water, for 5 minutes with a 1% HCl solution, for 2×5 minutes with an aqueous 1 M NaCl solution, and for 10 minutes with running water, to obtain membranes having iminodiacetic acid ligands (IDA membranes).

Example 10

Introduction of Phenyl Ligands (Ph Membrane)

Activatingly crosslinked membranes (intermediate products) were treated for three hours at room temperature with an aqueous solution of 1% aniline in a 0.1 M potassium phosphate (KPi) buffer at a pH of 8.0, and the moist samples were left for 19 hours in a sealed vessel. 15 minutes of rinsing with running water were followed by rinsing for 15 minutes with a 1 M aqueous NaCl solution and for 15 minutes with running water, to obtain membranes having phenyl ligands (Ph membranes).

Example 11

Introduction of p-aminobenzamidine Ligands (pABA Membrane)

A nonactivatingly crosslinked cellulose hydrate membrane (intermediate product) according to example 6 was activated by a 30-minute treatment with a 1% aqueous solution of sodium periodate at room temperature, rinsed for 15 minutes with running water, treated for one hour at room temperature with a solution, adjusted to a pH of 5.6, of 4.3 g of p-aminobenzamidine dihydrochloride,
2.17 g of sodium cyanoborohydride,
2 g of a 1 M sodium hydroxide solution, and
34.8 g of McIlvaine buffer having a pH of 5.6 (mixture of 0.1 M citric acid monohydrate (Riedel-de-Haen cat. 33114) and 0.2 M disodium hydrogen phosphate dihydrate (Merck cat. 1.06580). Dissolve 21 g of citric acid monohydrate in 1 l of reverse-osmosis water (ROW)=0.1 M. Dissolve 35.6 g of disodium hydrogen phosphate dihydrate in 1 l of ROW=0.2 M. Introduce 500 g of 0.2 M disodium hydrogen phosphate dihydrate, and adjust pH to 5.6 with 0.1 M citric acid monohydrate), rinsed for 15 minutes with running water, treated in succession with 100 g of a 1% aqueous NaBH$_4$ solution and 100 g of a 1 M aqueous NaCl solution, and rinsed again for 15 minutes with running water. As a result, membranes having p-aminobenzamidine ligands (pABA membranes) were obtained.

Example 12

Introduction of Cibacron Blue 3GA Ligands (CB Membrane)

A nonactivatingly crosslinked cellulose hydrate membrane (intermediate product) according to example 6 was treated for 24 hours at room temperature with a solution produced by admixing a 2% aqueous Cibacron Blue 3GA dye solution which had been stirred for 10 minutes at 80° C. and admixed at room temperature with a 3% aqueous sodium hydroxide solution, and rinsed successively for 60 minutes with running water, four times, for thirty minutes each time, with water at 80° C., and for 15 minutes with running water. As a result, membranes having Cibacron Blue 3GA ligands (CB membranes) were obtained.

Example 13

Drying of the Adsorption Membranes According to the Invention

CA membranes were hydrolyzed in a 0.5 M aqueous sodium hydroxide solution for 30 minutes at room temperature, subsequently, without rinsing, crosslinked with a solution of 30% 1,4-butanediol diglycidyl ether and 0.1% sodium borohydride in a 0.5 M aqueous sodium hydroxide solution at room temperature for 2.5 hours, then derivatized with trimethylamine, and investigated with regard to their static binding capacity both in an undried state and in a dried state, having been dried at 80° C. in a circulating air drying cabinet. The results are reported in table 2.

Example 14

Determination of the Fraction of Ultrapores of the Entire Pore Volume of the Membranes To determine the fraction of ultrapores of the entire pore volume of the membranes, the CA membrane was hydrolyzed analogously to example 2 at different sodium hydroxide solution concentrations, rinsed with 0.5 M NaOH, crosslinked as in example 2, and modified with sulfonic acid ligands as in example 8 (membranes 1-6). For comparison, the membrane from example 1 (membrane A) and the microfiltration membranes, known in the prior art, from Sartorius Stedim Biotech GmbH having pore sizes in the range 0.2-0.45 μm (membranes B-F) were used.

The Blue Dextran used was commercially available dextran from Leuconostoc mesenteroides, strain B 512, modified with Reactive Blue 2 dye, about 0.1 mmol of Reactive Blue 2 per gram of dextran (Blue Dextran Molecular Weight (Mw) 2 000 000 from Sigma, St. Louis, Mo., USA, product number D 5751, CAS number: 87915-38-6).

The hydrodynamic diameter d of this Blue Dextran can be calculated with the help of the Mark-Houwink-Sakurada equation:

$$d[\text{nm}] = 0.054 \times Mw^{0.5}$$

and is 76.4 nm.

Ultrapores are, as defined above, pores which are not accessible to Blue Dextran.

The pore volume accessible to water is referred to as Vw [cm$^3$]. It is assumed that all membrane pores are accessible to water, and therefore Vw corresponds to the entire pore volume of the membrane.

The pore volume accessible to Blue Dextran is referred to as Vd [cm$^3$].

The pore volume of the ultrapores not accessible to Blue Dextran is referred to as Vp [cm$^3$].

Vp is increased by the method according to the invention, in which the cellulose ester membrane swells during the hydrolysis.

The following equations apply: Vw=Vd+Vp and Vp=Vw−Vd

The percentage of pores inaccessible to Blue Dextran in the membrane is % Vp=100×(Vw−Vd)/Vw.

The pore volume Vd accessible to Blue Dextran is determined by the following method:

10 ml of a solution of Blue Dextran in RO water of a known concentration (c0) are filtered through a wet membrane. As a result, the water from the pore volume accessible to Blue Dextran is replaced with the Blue Dextran solution. The prerequisite for the technique is that the membrane does not adsorptively bind the Blue Dextran. This is the case for unmodified cellulose hydrate membranes, crosslinked and uncrosslinked. A membrane having a diameter of 50 mm (i.e., an area of 19.6 cm$^2$) is intensively washed for 15 minutes with running RO water. The wet membrane is then incorporated into a filtration housing, and 10 ml of Blue Dextran solution having a concentration of 5 mg/ml (c0) are filtered through the membrane at a pressure of 0.1 bar. The membrane is then removed from the filtration housing, a section having a diameter of 47 mm (i.e., an area of 17.3 cm$^2$) is punched out of the middle (in order to remove the sealed edges of the membrane) and dabbed dry with a laboratory towel (Kimtech Science, 200, 2, 21×20 cm, white, 7101).

Afterwards, the membrane is shaken in an exactly determined amount (volume V=5.0 ml) of RO water in a sealed vessel for 20 hours at 80 rpm. The concentration of the Blue Dextran solution (c) is then determined photometrically at 618 nm. The extinction coefficient E (1 mg/ml; 1 cm) of the Blue Dextran solution is 0.896. From the concentration of the Blue Dextran solution, the pore volume accessible to Blue Dextran is calculated:

$$Vd\ [\text{cm}^3] = c \times V/c0$$

The pore volume accessible to water is determined by the following method:

The membrane sample is intensively washed for 15 minutes with running RO water. The water adhering to the membrane is dabbed off with the laboratory towel, and the wet membrane is weighed. Afterwards, the membrane is dried at 80° C. in a circulating air drying cabinet for 30 minutes, and the dried membrane is weighed. The weight difference between the wet membrane and dry membrane corresponds to the amount of water in the membrane (Vw). A water density of 1.0 g/cm$^3$ is assumed.

$$\text{From \% } Vp = 100 \times (Vw - Vd)/Vw$$

the percentage of the pore volume not accessible to Blue Dextran in the entire pore volume is calculated.

With increasing sodium hydroxide solution concentration in the hydrolysis of the cellulose acetate membrane, the swelling becomes stronger, the degree of swelling increases, the permeability of the membrane decreases, the membrane thickness increases, the fraction of ultrapores of the entire pore volume increases, and the binding capacity increases, as is apparent from table 1 below.

TABLE 1

| | Hydrolysis c (NaOH) [M] | Rinsing after hydrolysis c (NaOH) [M] | Vp [%] | Permeability 10 mM KPi, pH 7 S membrane [ml/(min × bar × cm$^2$)] | Binding capacity of lysozyme S membrane [mg/cm$^2$] | Degree of swelling [—] |
|---|---|---|---|---|---|---|
| 1 | 0.20 | 0.5 | 16% | 515 | 0.75 | 1.4 |
| 2 | 0.40 | 0.5 | 25% | 341 | 1.40 | 2.1 |
| 3 | 0.50 | 0.5 | 30% | 180 | 1.71 | 4.1 |
| 4 | 0.60 | 0.5 | 34% | 73 | 1.99 | 10.0 |
| 5 | 0.75 | 0.5 | 39% | 8 | 2.23 | 90.1 |
| 6 | 1.00 | 0.5 | 45% | 4 | 2.40 | 208.6 |

Evaluation of the Membranes (For Examples 1 to 14 and Comparative Examples 1 and 2)

The membranes obtained were evaluated in the manner described below:

1) Flow Rate Determination

Membranes having an active membrane area of 12.5 cm$^2$ were each incorporated into a housing, and the time taken for the filtration of 100 ml of water or buffer was measured. The flow rate figures reproduced in table 2 for membranes reacted with functional groups relate to the corresponding binding buffer. The same buffers were used as for the determination of the binding capacities described below.

2) Determining the Static Binding Capacity of Q Membranes

Membrane samples having, in each case, an active membrane area of 17.6 cm$^2$ were shaken in 35 ml of 20 mM Tris/HCl, pH 7.3, for 3×5 minutes at about 80 revolutions per minute (rpm). Afterwards, the membrane samples were shaken in 35 ml of a solution of 2 mg/ml bovine serum albumin (BSA) solution in 20 mM Tris/HCl, pH 7.3, for 12-18 hours at 20-25° C. at about 80 rpm. Subsequently, the membrane samples were rinsed for 2×15 minutes in, in each case, 35 ml of 20 mM Tris/HCl, pH 7.3. Afterwards, the membrane samples were shaken in 20 ml of 20 mM Tris/HCl, pH 7.3+1 M aqueous NaCl solution. The amount of the eluted protein was determined by measurement of the optical density (OD) at 280 nm.

3) Determining the Static Binding Capacity of S Membranes

Membrane samples having, in each case, an active membrane area of 17.6 cm$^2$ were shaken in 35 ml of 10 mM KPi, pH 7.0, for 3×5 minutes at about 80 rpm. Afterwards, the membrane samples were shaken in 35 ml of a solution of 2 mg/ml lysozyme in 10 mM KPi, pH 7.6, for 12-18 hours at 20-25° C. at about 80 rpm. Subsequently, the membrane samples were rinsed for 2×15 minutes in, in each case, 35 ml of 10 mM KPi, pH 7.0. Afterwards, the membrane samples were shaken in 20 ml of 10 mM KPi, pH 7.0+1 M aqueous NaCl solution. The amount of the eluted protein was determined by measurement of the optical density (OD) at 280 nm.

4) Determining the Static Binding Capacity of IDA Membranes

Membrane samples having an active membrane area of 17.6 cm$^2$ were shaken in 35 ml of 10 mM KPi, pH 7.0, for 3×5 minutes at about 80 rpm. Afterwards, the membrane samples were shaken in 35 ml of a solution of 2 mg/ml lysozyme in 10 mM KPi, pH 7.0, for 12-18 hours at 20-25° C. at about 80 rpm. Subsequently, the membrane samples were rinsed for 2×15 minutes in, in each case, 35 ml of 10 mM KPi, pH 7.0. Afterwards, the membrane samples were shaken in 20 ml of 10 mM KPi, pH 7.0+1 M aqueous NaCl solution. The amount of the eluted protein was determined by measurement of the optical density (OD) at 280 nm.

5) Determining the static binding capacity of metal chelate membranes (iminodiacetic acid ligand (IDA) complexed with $Cu^{2+}$ cations)

IDA membrane samples having an active membrane area of 3.1 cm$^2$ were clamped into a polycarbonate attachment and connected to a peristaltic pump. 10 ml of each solution were each pumped in the following order through the membranes with the help of the peristaltic pump at a flow rate of 2 ml/min:

1. 0.1 M $CH_3COONa$+0.5 M NaCl, pH 4.5
2. 0.1 M $CH_3COONa$+0.5 M NaCl, pH 4.5+0.1 M $CuSO_4$
3. 0.1 M $CH_3COONa$+0.5 M NaCl, pH 4.5
4. 0.05 M KPi+0.5 M NaCl, pH 7.5
5. 2 mg/ml cytochrome C in 0.05 M KPi+0.5 M NaCl, pH 7.5
6. 0.05 M KPi+0.5 M NaCl, pH 7.5
7. 0.1 M imidazole in 0.05 M KPi+0.5 M NaCl, pH 7.5
8. 1 M $H_2SO_4$ The amount of the eluted protein in step 7 was determined by measurement of the optical density (OD) at 528 nm.

6) Determining the Static Binding Capacity of Ph Membranes

Membrane samples having an active membrane area of 3.1 cm$^2$ were clamped into a polycarbonate attachment and connected to a peristaltic pump. Solutions were pumped in the following order through the membranes with the help of the peristaltic pump at a flow rate of 2 ml/min:

1. 10 ml of 0.05 M KPi+1 M $(NH_4)_2SO_4$ NaCl, pH 7.0
2. 20 ml of 1 mg/ml gamma-globulin in 0.05 M KPi+1 M $(NH_4)_2SO_4$ NaCl, pH 7.0
3. 20 ml of 0.05 M KPi+1 M $(NH_4)_2SO_4$ NaCl, pH 7.0
4. 10 ml of 0.05 M KPi, pH 7.0

The amount of the eluted protein in step 4 was determined by measurement of the optical density (OD) at 280 nm.

7) Determining the Static Binding Capacity of pABA Membranes

Membrane samples having an active membrane area of 3.1 cm$^2$ were clamped into a polycarbonate attachment and connected to a peristaltic pump. Solutions were pumped in the following order through the membranes with the help of the peristaltic pump at a flow rate of 2 ml/min:

1. 10 ml of 50 mM Tris/HCl, pH 8.8+10 mM $CaCl_2$+250 mM NaCl
2. 10 ml of 2 mg/ml trypsin type I in 50 mM Tris/HCl, pH 8.8+10 mM $CaCl_2$+250 mM NaCl
3. 10 ml of 50 mM Tris/HCl, pH 8.8+10 mM $CaCl_2$+250 mM NaCl
4. 10 ml of 0.1 M glycine/HCl, pH 2.8

The amount of the eluted trypsin in step 4 was determined by trypsin determination according to Bergmeyer by the following method. The enzymatic activity of trypsin is determined as ΔA/min through the change in absorbance of N-α-benzoyl-L-arginine ethyl ester hydrochloride (BAEE) at a wavelength of 253 nm in the hydrolysis catalyzed by trypsin.

In a semi-micro quartz cuvette, the following solutions are mixed in the specified order:
1. 850 μl of buffer (50 mM Tris/HCl, pH 8.8+10 mM $CaCl_2$+250 mM NaCl),
2. 100 μl of BAEE solution in binding buffer (Sigma cat. no. B 4500), and
3. 50 μl of sample.

The filled cuvette is placed in a photometer, and ΔA/min is determined at 253 nm after 5 seconds.

8) Determining the Static Binding Capacity of CB Membranes

Membrane samples having an active membrane area of 9.8 cm² were shaken in 10 ml of a 0.1 M aqueous sodium hydroxide solution for 10 minutes and then shaken in 10 ml of 10 mM KPi, pH 7.3, for 3×10 minutes at about 80 rpm. Afterwards, the membrane samples were shaken in 5 ml of a solution of 2 mg/ml bovine serum albumin (BSA) in 10 mM KPi, pH 7.0, for 12-18 hours at 20-35° C. at about 80 rpm. Subsequently, the membrane samples were rinsed for 3×10 minutes in, in each case, 10 ml of 10 mM KPi, pH 7.0. Afterwards, the membrane samples were shaken for one hour in 5 ml of 10 mM KPi, pH 7.0+1 M aqueous NaCl solution. The amount of the eluted protein was determined by measurement of the optical density (OD) at 280 nm.

9) Confocal Laser Scanning Microscopy

Labeling the Membranes

An adsorption membrane from example 1 and an adsorption membrane according to the invention as per example 2 were provided with sulfonic acid ligands according to example 8. Together with an adsorption membrane from Sartorius Stedim Biotech GmbH, commercially available under the trade name Sartobind® S, having a sulfonic-acid-overlaid auxiliary polymer, the membranes were labeled with the OH-reactive fluorescent dye "5-DTAF" (5-(4,6-dichlorotriazinyl)aminofluorescein, excitation wavelength and emission wavelength of 492 nm and 516 nm respectively, Invitrogen). The incubation of the solution of the dye and also all following wash steps were carried out with, in each case, three membrane samples (diameter: 13 mm) in a filter holder with continuous rinsing at a flow rate of about 1 ml/minute. Use was made, in each case, of 20 ml of a 5-DTAF solution in a 100 mM sodium hydrogen carbonate solution having a pH of 9.3 and having concentrations matched to the membrane, viz. 13.5 μg/ml 5-DTAF+100 mM NaCl solution for the membranes according to examples 1 and 2, and 25 μg/ml 5-DTAF+200 mM NaCl solution for the Sartobind® S membrane. Since it was suspected that the three-dimensional cation exchanger layer causes particularly effective shielding of the cellulose matrix, both the dye concentration and salt concentration were increased for the Sartobind® S membrane. After rinsing for about 18 hours, the samples were subsequently washed in succession with, in each case, 100 ml of a 20% ethanol solution, a 1 M NaCl solution, and a 200 mM sodium phosphate buffer, pH 7.0. For the CLSM analysis, the second sample in the filter holder was used in each case because it had the best homogeneity of labeling.

Labeling and Cleanup of the Protein

Lysozyme (available from Sigma, St. Louis, Mo., USA; protein about 95%, about 50 000 units/mg of protein) was labeled with the $NH_2$-reactive fluorescent dye "Cy5 mono-Reactive NHS Ester" (available from GE Health Care Bio-Sciences AB, Uppsala, Sweden) in a sodium carbonate buffer, pH 9.3, and also subsequently cleaned up, firstly by gel filtration and then by HP ion exchange chromatography. By appropriate selection of the chromatographic fractions, the singly labeled lysozyme was obtained in a pure form. Afterwards, concentration was effected by means of ultrafiltration, to the concentration necessary for the binding experiment. The concentration of the labeled lysozyme was determined by means of a UV-Vis photometer (measurement of the absorbances at 280 nm and 650 nm).

Incubation of the Membranes with Protein

Samples of the membranes labeled with 5-DTAF were punched out with a diameter of 5 mm and incubated for four hours in a solution of the labeled lysozyme having a concentration of 0.6 g/L in a 200 mM sodium phosphate buffer, pH 7.0+50 mM aqueous NaCl solution (for 1 cm² samples, 4.1 ml of protein solution were used in each case). Afterwards, the samples were washed with the buffer for 15 minutes.

CLSM Analysis

The analysis was effected with the CLSM system Leica TCS SP. Each sample was examined in a 200 mM sodium phosphate buffer from both surfaces. Firstly, a suitable signal amplification was determined (criteria: suppressed autofluorescence of the membrane; the maximum of the signal amplification was set with the help of the histogram in the evaluation software "Zeiss LSM Image Browser" in order to avoid local overexposure) and z=0 was identified (criteria: high scattering intensity and subsequent first identification of the pore morphology with further reduction of the distance to the sample). Afterwards, the characteristic morphology of the Sartobind® S membranes known from SEM was searched for in x,y-scans at different z-positions. Afterwards, detailed x,y-scans of the two excitation wavelengths (488 nm for 5-DTAF, 633 nm for Cy5) were carried out in a narrow range of different z-positions (at a depth of about 20 micrometers, at intervals of 1 micrometer in both directions). For each sample and each orientation, these scans were carried out, in each case, for three different positions. The Sartobind® S sample was analyzed first; the settings chosen for this sample (z-position and signal amplification) were retained for the analysis of the other membrane samples. Because the signal intensities of the membrane according to the invention as per example 2 were very much higher at 633 nm than for the other two membranes, a reduction of the signal amplification was made:

"Gains" (488 nm/633 nm)

Sartobind® S membrane: 426/643

Membrane according to example 1: 426/669

Membrane according to example 2: 357/650

CLSM Evaluation

The evaluations were carried out with the help of the Zeiss LSM Image Browser 3.5.0.376. From the images obtained, detailed x,y-scans in a range of the z-positions of a depth of about 20 μm for the upper side were selected. The images obtained were each displayed as 8-bit images having a resolution of 512×512 pixels, corresponding to 146.2×146.2 μm². FIGS. 2 to 4 show the overlapping of the two images of the distribution of lysozyme and of the pore morphology of the cellulose. Additionally, an intensity profile of the intensities for both fluorescent labels is also shown for each measurement at the upper right edge of the picture.

Results of the Experiments

The results of the experiments are shown in table 2 below.

TABLE 2

| Membrane from example | Remark | Ligand | Protein | Flow rate | Binding capacity |
|---|---|---|---|---|---|
| 1 | | Q | BSA | 643 | 0.07 |
| | | S | Lysozyme | 664 | 0.01 |
| | | IDA | Lysozyme | 681 | 0.03 |
| | | IDA + Cu2+[1)] | Cytochrome C | 681 | 0.15 |
| | | Ph | Gamma-globulin | 570 | 0.2 |
| 2 | | Q | BSA | 44 | 0.92 |
| | | S | Lysozyme | 38 | 2.06 |
| | | IDA | Lysozyme | 41 | 1.91 |
| | | IDA + Cu2+[1)] | Cytochrome C | 41 | 0.5 |
| | | Ph | Gamma-globulin | 31 | 1.26 |
| 3 | | Q | BSA | 20 | 1.13 |
| | | S | Lysozyme | 24 | 2.85 |
| 4 | | Q | BSA | 158 | 0.74 |
| | | S | Lysozyme | 167 | 3.11 |
| | | S | Gamma-globulin | 167 | 0.44 |
| 5 | LiOH | Q | BSA | 70 | 1.18 |
| | NaOH | Q | BSA | 109 | 0.93 |
| | KOH | Q | BSA | 519 | 0.08 |
| 6 | | CB | BSA | 30 | 0.31 |
| | | pABA | Trypsin | 35 | 0.75 |
| 13 | Undried | Q | BSA | 213 | 0.94 |
| | Dried | Q | BSA | 239 | 0.92 |

[1)]Metal chelate of iminodiacetic acid ligand (IDA) complexed with $Cu^{2+}$ cations.

Comparative Example 1

Simultaneous hydrolysis and crosslinking as in example 1, sample K10C of WO 2007/017085 A2, but with 1,4-butanediol diglycidyl ether instead of epichlorohydrin, under nonswelling conditions.

A CA membrane as defined above and a 0.65 μm cellulose acetate membrane as in example 1, sample K10C of WO 2007/017085 A2 having a water flow rate of 65 ml/(min×bar×cm²) were used as starting membranes.

The cellulose acetate membranes were heated to 47° C. in 100 g of water, 10 g of $Na_2SO_4$, and 1 g of 1,4-butanediol diglycidyl ether, and 10 g of a 1 M aqueous sodium hydroxide solution were metered in over 30 minutes. The membranes were further treated in the solution for 3.5 hours at 47° C. and subsequently rinsed for 30 minutes with running water. Quaternary ammonium ligands were introduced into the membranes to obtain Q membranes. The hydrolyzed and crosslinked Q membrane obtained from the CA membrane exhibited a water flow rate of 589 ml/(min×bar×cm²), a degree of swelling of 1.2, and a binding capacity for BSA of 0.04 mg/cm². The hydrolyzed and crosslinked Q membrane obtained from the cellulose acetate membrane according to example 1, sample K10C of WO 2007/017085 A2 exhibited a water flow rate of 66 ml/(min×bar×cm²), a degree of swelling of 1.0, and a binding capacity for BSA of 0.04 mg/cm².

Comparative Example 2

Attempt to Swell Previously Hydrolyzed Cellulose Hydrate Membranes

A CA membrane as defined above and used as a starting membrane was hydrolyzed for three minutes at room temperature with a 15% potassium hydroxide solution in 80% ethanol and subsequently rinsed for three minutes with a 6.8% acetic acid solution, twice with ethanol, and for 15 minutes with running RO water. The hydrolyzed membrane obtained was treated for 30 minutes at room temperature with a 0.6 M aqueous sodium hydroxide solution and then rinsed three times for 10 minutes with a 0.5 M aqueous sodium hydroxide solution. Subsequently, the membrane was treated for 30 minutes at room temperature with a 30% solution of 1,4-butanediol diglycidyl ether in a 0.1 M aqueous sodium hydroxide solution and 0.1% aqueous sodium borohydride solution, whereupon the moist membrane was left to stand for 20 hours in a closed vessel at room temperature. Finally, the membrane obtained was rinsed for 30 minutes with running water.

The water flow rate of the hydrolyzed and crosslinked cellulose hydrate membrane thus produced was 688 ml/(min×bar×cm²), and the degree of swelling was 1.06.

Quaternary ammonium ligands or sulfonic acid ligands were, as described in examples 7 or 9, introduced into two samples of the membrane to obtain a Q membrane and an S membrane. The Q membrane exhibited a binding capacity for BSA of 0.044 mg/cm², and the S membrane exhibited a binding capacity for lysozyme of 0.067 mg/cm².

Examples of the Membranes According to the Invention with Functionalization by Polyamines Example 15

Functionalization by Polyethyleneimine

The CA membrane was hydrolyzed for 30 minutes at room temperature with a 0.6 M aqueous sodium hydroxide solution (i.e., under swelling* conditions) and subsequently rinsed for 3×10 minutes with a 0.5 M aqueous sodium hydroxide solution. The membrane obtained was treated for 30 minutes at room temperature with 30% 1,4-butanediol diglycidyl ether in a 0.1 M aqueous sodium hydroxide solution and 0.1% aqueous sodium borohydride solution (i.e., crosslinked and provided with reactive epoxy groups), and the moist membrane was then left to stand for 20 hours in a closed vessel at room temperature. Finally, it was rinsed for 30 minutes with running water.

500 cm² membranes were each treated in 500 g of a 50% solution of Lupasol® FG (polyethyleneimine (PEI) from BASF AG, CAS number 25987-06-8, molar mass of 800 g/mol) in RO water (reverse-osmosis water) for 1 hour at 50° C. The membranes were subsequently treated for 5 minutes at room temperature with a 5% sulfuric acid solution and then rinsed for 10 minutes with running water.

* The swelling of the cellulose ester matrix during the hydrolysis of the ester groups is described by the degree of swelling, i.e., the ratio of the water permeability of the cellulose ester membrane wetted beforehand with water to the water permeability of the final, i.e., hydrolyzed, cellulose hydrate membrane, which has optionally been activatingly crosslinked and provided with ligand(s).

Example 16

Functionalization by Polyethyleneimine

The CA membrane was hydrolyzed, crosslinked, and provided with reactive epoxy groups as in example 15. 500 cm² membranes were each treated in 500 g of a 30% solution of Lupasol® WF (polyethyleneimine from BASF AG, molar mass of 25 000 g/mol) in RO water for 1 hour at 50° C. The membranes were subsequently treated for 5 minutes at room temperature with a 5% sulfuric acid solution and then rinsed for 10 minutes with running water.

Example 17

Functionalization by Polyethyleneimine

The CA membrane was hydrolyzed, crosslinked, and provided with reactive epoxy groups as in example 15. 500 cm$^2$ membranes were each treated in 500 g of a 20% solution of Lupasol® PN 50 (polyethyleneimine from BASF AG, molar mass of 1 000 000 g/mol) in RO water for 1 hour at 50° C. The membranes were subsequently treated for 5 minutes at room temperature with a 5% sulfuric acid solution and then rinsed for 10 minutes with running water.

Example 18

Functionalization by Polyethyleneimine, Immobilized via Aldehyde Groups

The CA membrane was hydrolyzed and activated as in example 15. Afterwards, the membrane was treated with a 5% sulfuric acid solution for 3 hours at 50° C. Subsequently, the membrane was treated for 30 minutes with a 1% aqueous NaIO$_4$ solution and rinsed for 15 minutes with running RO water. 500 cm$^2$ membranes were treated with 500 g of a solution of 20% Lupasol® WF (BASF AG, molar mass of 25 000 g/mol) and 0.3% NaBH$_4$ in RO water for 2 hours at 22° C. The membrane was further treated for 15 minutes with 1% NaBH$_4$ in RO water in order to reduce residual aldehyde groups. The membrane was further rinsed for 15 minutes with running RO water, treated for 5 minutes at room temperature with a 5% sulfuric acid solution, and then rinsed for 10 minutes with running water.

Example 19

Functionalization by Polyvinylamine

The CA membrane was hydrolyzed, crosslinked, and provided with reactive epoxy groups as in example 15. 500 cm$^2$ membranes were treated in 500 g of a 10% solution of Lupamin® 1595 (polyvinylamine from BASF AG, molar mass of ~10 000 g/mol) in a 32% solution, by weight, of NaOH in RO water at a pH of 12.0 for 1 hour at 50° C. The membranes were subsequently treated for 5 minutes at room temperature with a 5% sulfuric acid solution and then rinsed for 10 minutes with running water.

Example 20

Functionalization by Polyvinylamine

The CA membrane was hydrolyzed, crosslinked, and provided with reactive epoxy groups as in example 15. 500 cm$^2$ membranes were treated in 500 g of a 5% solution of Lupamin® 9095 (polyvinylamine from BASF AG, molar mass of ~430 000 g/mol) in a 32% solution, by weight, of NaOH in RO water at a pH of 12.0 for 1 hour at 50° C. The membranes were subsequently treated for 5 minutes at room temperature with a 5% sulfuric acid solution and then rinsed for 10 minutes with running water.

Example 21

Functionalization by Polyallylamine

The CA membrane was hydrolyzed and activated as in example 15. 500 cm$^2$ membranes were treated with 500 g of a 20% solution of polyallylamine (Nitto Boseki, molar mass of 15 000 g/mol) in RO water for 1 hour at 50° C. The membranes were subsequently treated for 5 minutes at room temperature with a 5% sulfuric acid solution and then rinsed for 10 minutes with running water.

Example 22

Functionalization by Polyallylamine

The CA membrane was hydrolyzed and activated as in example 15. 500 cm$^2$ membranes were treated with 500 g of a 20% solution of polyallylamine (Nitto Boseki, molar mass of 150 000 g/mol) in RO water for 1 hour at 50° C. The membranes were subsequently treated for 5 minutes at room temperature with a 5% sulfuric acid solution and then rinsed for 10 minutes with running water.

Example 23

Functionalization by Polyethyleneimine Having Hydrophobic Functionalities

The membrane was produced as in example 15. Afterwards, the membrane was treated with 220 g of a solution of 5 g of phenyl glycidyl ether in 190 g of a 60% ethanol solution (60% by weight of ethanol, 40% by weight of RO water) for 1 hour at 40° C. The membrane was subsequently treated for 2×10 minutes at room temperature with a 5% sulfuric acid solution, for 10 minutes with a 1 M NaCl solution, and also for 2×5 minutes with ethanol, and then rinsed for 10 minutes with running water.

Comparative Example 3

Checking the Covalent Bonding

In order to check whether the polyamines are covalently bonded to the membrane, the epoxy groups were hydrolyzed prior to the reaction with polyethyleneimine and, as a result, deactivated. The CA membrane was hydrolyzed and activated as in example 15. Afterwards, the membrane was treated with a 5% sulfuric acid solution for 3 hours at 50° C. and reacted with Lupasol® WF as in example 16.

Charge density, example 16: 30.1 µeq/cm$^2$

Charge density, comparative example 3: 0.9 µeq/cm$^2$

Comparative Example 4

Functionalization of the Membrane with Polyethyleneimine via an Epoxy-Group-Comprising Polymer Grafted to the Membrane A cellulose hydrate membrane was grafted with glycidyl methacrylate according to EP 0 527 992 B1 (example 1, coating concentration of 0.2%, 5% glycidyl methacrylate, 0.1% sodium dithionite, duration of grafting of 10 minutes) and subsequently rinsed with acetone and running RO water.

This membrane was treated with a 40% aqueous solution of Lupasol® FG (polyethyleneimine (PEI) from BASF AG, CAS number 25987-06-8, molar mass of 800 g/mol) using 1 g of solution per square centimeter of membrane for 1 hour at 50° C. The membrane was subsequently treated for 5 minutes at room temperature with a 5% sulfuric acid solution and then rinsed for 10 minutes with running water.

The results of the experiments with polyamine functionalization are shown in table 3 below.

TABLE 3

| Membrane | Polymeric amine | Mw [g/mol] | Flow rate [ml/(min*bar*cm²)] | BSA* Capacity [mg/cm²] | Charge density [µeq/cm²] | DNA binding [mg/cm²] |
|---|---|---|---|---|---|---|
| Example 15 | Lupasol ® FG | 800 | 175 | 1.37 | 15.1 | 0.84 |
| Example 16 | Lupasol ® WF | 25 000 | 161 | 1.28 | 30.1 | 1.9 |
| Example 17 | Lupasol ® PN 50 | 1 000 000 | 85 | 1.98 | 12.6 | 1.12 |
| Example 18 | Lupasol ® WF | 25 000 | 168 | 0.98 | 16.7 | 0.68 |
| Example 19 | Lupamin ® 1595 | 10 000 | 224 | 0.80 | 9.7 | 0.51 |
| Example 20 | Lupamine ® 9095 | 430 000 | 229 | 1.93 | 4.0 | 0.45 |
| Example 21 | Polyallylamine | 15 000 | 155 | 1.90 | 15.0 | 0.6 |
| Example 22 | Polyallylamine | 150 000 | 191 | 1.40 | 12.0 | 0.56 |
| Example 23 | Lupasol ® WF | 25 000 | 167 | 0.99 | 13.2 | — |
| Comparison with Sartobind ® Q | — | — | 228 | 0.97 | 3.0 | 0.18 |
| Comparative example 3 | Lupasol ® WF | 25 000 | 173 | — | 0.9 | — |
| Comparative example 4 | Lupasol ® FG | 800 | 457 | 0.01 | 14.2 | 0.04 |

*BSA: Bovine serum albumin

Evaluation of the Membranes (For Examples 15 to 23 and Comparative Examples 3 and 4)

The membranes obtained were evaluated in the manner described below:

1) Flow Rate Determination

Membranes having an active membrane area of 12.5 cm² were each incorporated into a housing, and the time taken for the filtration of 100 ml of a 20 mM Tris/HCl buffer at pH 7.3 and at 0.1 bar was measured.

2) Determining the Static Binding Capacity

Membrane samples having, in each case, an active membrane area of 17.6 cm² were shaken in 35 ml of a 20 mM Tris/HCl buffer at pH 7.3 for 3×5 minutes at about 80 revolutions per minute (rpm). Afterwards, the membrane samples were shaken in 35 ml of a 2 mg/ml bovine serum albumin (BSA) solution (supplier: SERVA) in a 20 mM Tris/HCl buffer at pH 7.3 for 12-18 hours at 20-25° C. at about 80 rpm. Subsequently, the membrane samples were rinsed for 2 ×15 minutes with, in each case, 35 ml of a 20 mM Tris/HCl buffer at pH 7.3. Afterwards, the membrane samples were shaken in 20 ml of a 20 mM Tris/HCl buffer (pH 7.3)+1 M NaCl. The amount of the eluted protein was determined by measurement of the optical density (OD) at 280 nm.

3) Determining the Charge Density

Three layers of membrane were clamped into a membrane holder. The membrane stack had a membrane area of 15 cm², an inflow area of 5 cm², and a bed height (thickness of the membrane stack) of 750 µm in the membrane holder. The membranes in the membrane holder were flooded with a 20 mM Tris/HCl buffer at pH 7.4 in order to displace the air and then connected to an Äkta Explorer 100 FPLC system from General Electric Health Care.

Afterwards, the membranes, i.e., the membrane stack, were examined with regard to their charge density with a test program comprising four steps. The four steps of the test program are specified below:
1. Conditioning the membrane with 6 ml of a 1 M NaCl solution in 20 mM Tris/HCl at pH 7,
2. Regenerating the membrane with 6 ml of a 1 M solution of NaOH in RO water,
3. Washing the membrane with 88 ml of RO water, and
4. Loading the membrane with 21 ml of 10 mM HCl All steps were carried out at a flow rate of 10 ml/min. In all steps, the conductivity in the detector behind the membrane unit was measured. The area above the breakthrough curve thus recorded was integrated after substraction of the dead volume, and the charge density was calculated from it.

4) Binding of DNA

Three layers of membrane from examples 15 to 22 were clamped into a membrane holder. The membrane stack had a membrane area of 15 cm², an inflow area of 5 cm², and a bed height (thickness of the membrane stack) of 750 µm in the membrane holder. The membranes in the membrane holder were flooded with 50 mM NaCl in a 20 mM Tris/HCl buffer (pH 7.4) in order to displace the air and then connected to an Äkta Explorer 100 FPLC system from General Electric Health Care.

Afterwards, the membranes, i.e., the membrane stack, were examined with regard to DNA binding with a test program comprising two steps. The two steps of the test program are specified below:
1. Equilibrating the membrane with 10 ml of a 50 mM NaCl solution in a 20 mM Tris/HCl solution (pH 7.4)
2. Loading the membrane with 100 µg/ml salmon sperm DNA (supplier: VWR, product number 54653) in 50 mM NaCl in a 20 mM Tris/HCl solution until the concentration in the detector was 10% of the starting concentration.

All steps were carried out at a flow rate of 10 ml/min. In all steps, the absorbance at 260 nm in the detector behind the membrane unit was measured. The area above the breakthrough curve thus recorded was integrated after substraction of the dead volume, and DNA binding at 10% breakthrough was calculated from it.

5) Binding of Host Cell Proteins (HCPs)

To determine the binding of host cell proteins, a 10× concentrated HCP solution in PBS buffer (pH 7.4) without antibodies was used, produced at a contract manufacturer in a mock run (cultivation of a cell line without antibody production) of an ovarian cell line from Chinese hamster. The HCP solution was diluted 1:10 in a 20 mM Tris/HCl buffer (pH 7.4), and the conductivity was set to 10 mS/cm by adding NaCl. 1000 ml of the diluted HCP solution were used to load the membranes. The HCP concentration was determined with the help of an ELISA test (enzyme-linked immunosorbent assay ELISA Cygnus CM015) according to the manufacturer's instructions. The concentration of host cell proteins (HCPs) was 7 µg/ml.

Three layers of membrane from example 16 or 21 were clamped into a membrane holder. The membrane stack had a membrane area of 15 cm², an inflow area of 5 cm², and a bed height (thickness of the membrane stack) of 750 µm in the membrane holder. The membranes in the membrane holder were flooded with a 20 mM Tris/HCl buffer (pH 7.4) in order to displace the air and then connected to an Äkta Explorer 100 FPLC system from General Electric Health Care.

Afterwards, the membranes, i.e., the membrane stack, were examined with regard to HCP binding with a test program comprising four steps. The four steps of the test program are specified below:
1. Equilibrating the membrane with 10 ml of a 20 mM Tris/HCl buffer (pH 7.4) having a conductivity of 10 mS/cm,
2. Loading the membrane with a 100 ml HCP solution,
3. Washing with 10 ml of 20 mM Tris/HCl (pH 7.4, conductivity of 10 mS/cm), and
4. Eluting with 10 ml of 1 M NaCl in a 20 mM Tris/HCl buffer (pH 7.4).

All steps were carried out at a flow rate of 10 ml/min. In all steps, the absorbance at 280 nm in the detector behind the membrane unit was measured. The breakthrough curves are shown in FIG. 7.

6) Binding of Model Viruses

The bacteriophage ΦX174, having a diameter of about 30 nm and an isoelectric point pI of 6.4-6.7, was used as a model virus.
Phage: Bacteriophage ΦX174 (ATCC 13706-B1)
Host organism: *Escherichia coli* C (ATCC 13706);
Terms/Abbreviations:
pfu: Plaque forming units
LRV: Logarithmic reduction value
LF: Conductivity of the buffer solution
Phage Solution:

The phage strain of $10^{10}$ pfu/ml is stored at −70° C. The phages were diluted in the respective buffer such that a titer of $4 \times 10^7$ pfu/ml was present. Prior to loading the membrane samples, the starting solutions were filtered through a Sartopore® 2 membrane (0.1 μm).
Buffer A: 25 mmol/l Tris/HCl, pH 8.1, LF=1.38 mS/cm
Buffer B: 25 mmol/l Tris/HCl+50 mmol/l sodium chloride, pH 8.1, LF=6.7 mS/cm
Buffer C: 25 mmol/l Tris/HCl+150 mmol/l sodium chloride, pH 8.1, LF 16.8 mS/cm
Membranes:
Comparative Example: Sartobind° Q Membrane
Example 21: Polyallylamine
Example 16: Polyethyleneimine 30 mm disks were punched from the membrane samples and clamped in 3 layers into a membrane holder (LP15). The membrane stack had a membrane area of 15 cm², an inflow area of 5 cm², and a bed height (thickness of the membrane stack) of 750 μm in the membrane holder.
Calculations:

$$LRV = \log_{10}\left(\frac{C_{starting\ solution}}{C_{flow-through}}\right)$$

$C_{starting\ solution}$=Phage titer in the starting solution [pfu/ml]
$C_{flow-through}$=Phage titer in the flow-through [pfu/ml]
Procedure:

The experiments were carried out on a multichannel pump, in such a way that a membrane sample was incorporated into three LP15s and loaded in parallel with phages in buffer system A (without salt), B (with 50 mmol/l NaCl), and C (150 mmol/l NaCl). A volume of 800 ml of phage solution was filtered at a flow rate of 20 ml/min. The flow-through was collected in 200 ml fractions. Each experiment was carried out in duplicate. The starting solutions and the flow-throughs were diluted in a clean bench and combined with the host organism *Escherichia coli* C. After the incubation time of 10 minutes, the samples were plated out on agar and incubated overnight at 37° C. The next day, the plaques were counted and the titer calculated.

The results of the experiments are shown in table 4 below.

TABLE 4

| | LRV after 800 ml of phage solution having a titer of $4 \times 10^7$ pfu/ml | | |
|---|---|---|---|
| Membrane | 0 mmol/l NaCl | 50 mmol/l NaCl | 150 mmol/l NaCl |
| Comparative example Sartobind ® Q | 2.5 | 0 | 0 |
| Example 16 | 4.5 | 4 | 3.5 |
| Example 21 | 5 | 5 | 4.5 |

What is claimed is:

1. A crosslinked cellulose hydrate membrane having a porous double structure consisting of
   micropores having a diameter in the range from >100 nm to 20 μm, and
   ultrapores which have a diameter of <100 nm and which are not accessible to Blue Dextran having an average molecular weight Mw of 2 000 000, wherein the fraction of the volume of the ultrapores is more than 15% of the entire pore volume accessible to water,
   wherein the crosslinked cellulose hydrate membrane is obtained by a method comprising:
   providing a cellulose ester membrane having a pore diameter in the range from 0.1 to 20 μm;
   hydrolyzing the cellulose ester membrane under a swelling condition; and
   crosslinking the hydrolyzed cellulose ester membrane;
   wherein the hydrolysis and the crosslinking are carried out separately, and;
   the hydrolysis is carried out in a hydrolysis medium consisting of water and one or both of sodium hydroxide and lithium hydroxide, wherein the concentration of one or both of sodium hydroxide and lithium hydroxide in the hydrolysis medium is in the range of 0.4 to 10% by weight, based on the hydrolysis medium.

2. The crosslinked cellulose hydrate membrane as claimed in claim 1, wherein the micropores which stretch from a first main surface of the membrane through the membrane to a second main surface are connected with formation of channels communicating with one another, and the ultrapores stretch from an inner surface of the micropores into a material forming the structure of the membrane, forming a dead end, and/or connect neighboring micropores with one another.

3. The crosslinked cellulose hydrate membrane as claimed in claim 1, wherein at least one functional group is bonded to the membrane.

4. The crosslinked cellulose hydrate membrane as claimed in claim 3, wherein the at least one functional group is/are ligand(s) which is/are capable of entering into interactions with adsorbates present in fluids.

5. The crosslinked cellulose hydrate membrane as claimed in claim 4, wherein the ligands comprise anionic and cationic groups.

6. The crosslinked cellulose hydrate membrane as claimed in claim 5, wherein the cationic groups are selected from the group consisting of primary, secondary, tertiary, and/or quaternary amines.

7. The crosslinked cellulose hydrate membrane as claimed in claim 6, wherein the primary, secondary, and/or tertiary amines are polymeric compounds having linear and/or branched and/or cyclic structures.

8. The crosslinked cellulose hydrate membrane as claimed in claim 7, wherein the polymeric compounds are selected from the group consisting of polyalkyleneimines having a molar mass in the range from 800 to 1 000 000 g/mol.

9. The crosslinked cellulose hydrate membrane as claimed in claim 7, wherein the polymeric compounds are selected from the group consisting of polyallylamines having a molar mass in the range from 3000 to 150 000 g/mol.

10. The crosslinked cellulose hydrate membrane as claimed in claim 7, wherein the polymeric compounds are selected from the group consisting of polyvinylamines having a molar mass in the range from 5000 to 500 000 g/mol.

11. The crosslinked cellulose hydrate membrane as claimed in claim 7, wherein the polymeric compound is polymyxin B.

12. The crosslinked cellulose hydrate membrane as claimed in claim 7, wherein at least one primary, secondary, or tertiary amine group is reacted with a component selected from the group comprising phenyl glycidyl ether, 1,2-epoxyethylbenzene, dodecyl glycidyl ether, tetradecyl glycidyl ether, benzyl chloride, (3-glycidyloxypropyl)trimethoxysilane, bis[(4-glycidyloxy)phenyl]methane, bisphenol A diglycidyl ether, 1,4-butanediol diglycidyl ether, 6-hexanediol diglycidyl ether, N,Ndiglycidyl-4-glycidyloxyaniline, 4,4'-methylenebis(N,N-diglycidylaniline), and/or tris(4-hydroxyphenyl)methane triglycidyl ether.

13. The crosslinked cellulose hydrate membrane as claimed in claim 5, wherein the anionic groups are selected from the group consisting of sulfonic and carboxylic acids.

14. The crosslinked cellulose hydrate membrane as claimed in claim 4, wherein the ligands are affinity ligands.

15. The crosslinked cellulose hydrate membrane as claimed in claim 14, wherein the affinity ligands are selected from the group consisting of benzamidines, biomimetic ligands, and/or proteins.

16. The crosslinked cellulose hydrate membrane as claimed in claim 4, wherein the ligands are selected from the group consisting of metal chelates.

17. The crosslinked cellulose hydrate membrane as claimed in claim 4, wherein the ligands are selected from the group consisting of reactive epoxide, aldehyde, azlactone, N-hydroxysuccinimide, and/or carbodiimide groups.

18. The crosslinked cellulose hydrate membrane as claimed in claim 4, wherein the ligand is a catalyst.

19. The crosslinked cellulose hydrate membrane as claimed in claim 4, wherein at least two structurally different ligands are bonded to the membrane.

20. The crosslinked cellulose hydrate membrane as claimed in claim 3, wherein the at least one functional group is part of a spacer which is bonded to the cellulose hydrate membrane.

21. The crosslinked cellulose hydrate membrane as claimed in claim 20, wherein the spacer is an oligomer or a polymer.

22. A method for producing a crosslinked cellulose hydrate membrane having a porous double structure as claimed in claim 1, comprising:
providing a cellulose ester membrane having a pore diameter in the range from 0.1 to 20 μm,
optionally pretreating the cellulose ester membrane in a medium at a temperature in the range from about 20° C. to about 100° C, and
hydrolyzing the optionally pretreated cellulose ester membrane under swelling condition, wherein the hydrolysis is carried out in a hydrolysis medium consisting of water and one or both of sodium hydroxide and lithium hydroxide, wherein the concentration of one or both of sodium hydroxide and lithium hydroxide in the hydrolysis medium is in the range of 0.4 to 10% by weight, based on the hydrolysis medium, and
crosslinking the hydrolyzed cellulose ester membrane;
wherein the hydrolysis and the crosslinking are carried out separately.

23. The method as claimed in claim 22, wherein a temperature of the hydrolysis medium during the hydrolysis is in the range from 10° C up to a boiling point of the hydrolysis medium.

24. The method as claimed in claim 22, wherein the hydrolysis is carried out in a period in the range from about 0.1 to about 60 minutes.

25. The method as claimed in claim 22, wherein the crosslinking is carried out with at least one crosslinking agent which comprises at least 2 functional groups in a molecule which are reactive with hydroxyl groups of the cellulose.

26. The method as claimed in claim 25, wherein the crosslinking agent is selected from the group consisting of diepoxide compounds, diisocyanates, epichlorohydrin, epibromohydrin, dimethylurea, dimethylethyleneurea, dimethylchlorosilane, bis(2-hydroxyethyl) sulfone, divinyl sulfone, alkylene dihalogen, hydroxyalkylene dihalogen, and glycidyl ethers.

27. The method as claimed in claim 25, wherein the crosslinking agent is a diepoxide compound.

28. The method as claimed in claim 22, wherein the crosslinking is carried out in an aqueous medium, an organic solvent, or a mixture of water and an organic solvent.

29. The method as claimed in claim 22, wherein the crosslinking is carried out in the presence of a crosslinking catalyst.

30. The method as claimed in claim 28, wherein the crosslinking is carried out at a temperature in the range from about 4° C up to a boiling point of the crosslinking medium.

31. The method as claimed in claim 22, wherein the crosslinking is carried out in a period in the range from about 10 minutes to about 100 hours.

32. The method as claimed in claim 22, wherein functional groups become bonded to the membrane.

33. The method as claimed in claim 32, wherein the functional groups are introduced during or after crosslinking of the hydrolyzed membrane.

34. The method as claimed in claim 33, wherein the membrane is dried after introducing the functional groups.

35. The method as claimed in claim 32, wherein the functional groups are ligands which enter into interactions with adsorbates present in fluids.

36. The method as claimed in claim 34, wherein the membrane is dried from a medium which comprises a pore-stabilizing compound.

37. An apparatus for membrane chromatography, comprising at least one crosslinked cellulose hydrate membrane as claimed in claim 1.

38. The method as claimed in claim 22, wherein method further comprises: prior to the hydrolysis, optionally pretreating the cellulose ester membrane in a medium at a temperature in the range from about 20° C to about 100° C.

* * * * *

UNITED STATES PATENT AND TRADEMARK OFFICE
CERTIFICATE OF CORRECTION

PATENT NO.        : 9,433,904 B2
APPLICATION NO.   : 12/937847
DATED             : September 6, 2016
INVENTOR(S)       : Wolfgang Demmer et al.

It is certified that error appears in the above-identified patent and that said Letters Patent is hereby corrected as shown below:

In the Specification

In Column 1 at Line 7, Change "designing" to --designating--.

In Column 1 at Line 10, Change "2005." to --2008.--.

In Column 7 at Line 9, Change "cornpounds," to --compounds,--.

In Column 7 at Line 64, Change "agueous" to --aqueous--.

In Column 11 at Lines 9-10, Change "absorbents" to --adsorbents--.

In Column 11 at Line 56, Change "groupcomprising" to --group comprising--.

In Column 12 at Line 2, Change "epoxyactivated" to --epoxy activated--.

In Column 14 at Line 47 (approx.), Change "form ation" to --formation--.

In Column 14 at Lines 50-51 (approx.), Change "membrave" to --membrane--.

In Column 20 at Line 53, Change "McIlvaine" to --Mcilvaine--.

In Column 31 at Line 66, Change "substraction" to --subtraction--.

In Column 32 at Lines 42-43, Change "substraction" to --subtraction--.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,433,904 B2

In the Claims

In Column 35 at Line 27 (approx.), In Claim 12, change "Ndiglycidyl" to --N-diglycidyl--.